(12) United States Patent
McConnell et al.

(10) Patent No.: US 10,509,046 B2
(45) Date of Patent: Dec. 17, 2019

(54) DETECTION OF INDAZOLE SYNTHETIC CANNABINOIDS

(71) Applicant: Randox Laboratories Limited, Crumlin, Antrim (GB)

(72) Inventors: Ivan McConnell, Antrim (GB); Peter Fitzgerald, Antrim (GB); Philip Lowry, Antrim (GB); Elouard Benchikh, Antrim (GB)

(73) Assignee: Randox Laboratories Limited, Antrim (GB)

( * ) Notice: Subject to any disclaimer, the term of this patent is extended or adjusted under 35 U.S.C. 154(b) by 0 days.

(21) Appl. No.: 14/859,948

(22) Filed: Sep. 21, 2015

(65) Prior Publication Data

US 2016/0084859 A1  Mar. 24, 2016

(30) Foreign Application Priority Data

Sep. 19, 2014 (GB) .................................. 1416624.3
Sep. 22, 2014 (GB) .................................. 1416733.2

(51) Int. Cl.
| | | |
|---|---|---|
| *G01N 33/94* | (2006.01) | |
| *C07K 16/44* | (2006.01) | |
| *C07D 409/12* | (2006.01) | |
| *C07D 231/56* | (2006.01) | |

(52) U.S. Cl.
CPC ......... *G01N 33/948* (2013.01); *C07D 231/56* (2013.01); *C07D 409/12* (2013.01); *C07K 16/44* (2013.01)

(58) Field of Classification Search
CPC .... C07D 231/56; C07D 409/12; C07K 16/44; G01N 33/948
See application file for complete search history.

(56) References Cited

U.S. PATENT DOCUMENTS

2013/0196354 A1* 8/2013 Fitzgerald ............ C07D 209/12
435/7.92

OTHER PUBLICATIONS

C. V. Rao, "Immunology, a textbook", Alpha Science Internatl. Ltd., 2005, pp. 63, 69-71.*
Uchiyama et al., "New cannabimimetic indazole derivatives, N-(1-amino-3-methyl-1-oxobutan-2-yl)-1-pentyl-1H-indazole-3-carboxamide (AB-PINACA) and N-(1-amino-3-methyl-1-oxobutan-2-yl)-1-(4-fluorobenzyl)-1H-indazole-3-carboxamide (AB-FUBINACA) identified as designer drugs in illegal products," Forensic Toxicol., 2013, vol. 31, issue 1, pp. 93-100.*
"AB-PINACA Synthetic Cannabinoid ELISA Kit" dated Sep. 25, 2014 and posted on Internet on Sep. 26, 2014 (www.tulipbiolabs.com/webassets/4800_005datasheet.pdf.).*
Englebienne, "Immune and Receptor Assays in Theory and Practice," CRC Press, 2000, p. 308.*
Safety Data Sheet, "AB-PINACA pentanoic acid metabolite", Revision Feb. 5, 2016; Supersedes Revision Nov. 8, 2013.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Takayama, Takahiro et al., "UPLC/ESI-MS/MS-Based Deteremination of Metabolism of Several New Illicit Drugs, ADB-FUBINACA, AB-FUBINACA, AB-PINACA, QUPIC, 5F-QUPIC and a-PVT, by Human Liver Microsome, " Biomedical Chromatography, 2014; 28: 831-838.
Thermo Scientific Pierce Crosslinging Technical Handbook, Part of Thermo Fisher Scientific, 2009.
Randox "AB-PINACA: Enzyme-Linked Immunosorbent Assay," Randox Laboratories Limited, Elisa PAC 10046, Jun. 4, 2015, 6 pages.
Tulip BioLab Data Sheet #4800-005, 20150306, Ab-PINACA Synthetic Cannabinoid ELISA Kit, 3 pages, Accessed Nov. 1, 2016.
Tulip BioLabs Data Sheet #4700-005, 20160225, AKB48 (APINACA) Synthetic Cannabinoid ELISA Kit, 3 pages, Accessed Nov. 1, 2016.
Tulip BioLabs Data Sheet #9027, p. 1 of 1 (140314J). AKB48 N-Pentanoic Acid ELISA Standard, Cat. #9027, LotQ0000, Accessed Nov. 1, 2016.
Tulip BioLabs Data Sheet #9028, p. 1 of 1 (141016J), AB-PINACA N-Pentanoic Acid ELISA Standard, Cat. #9028, LotQ0000, Accessed Nov. 1, 2016.

* cited by examiner

*Primary Examiner* — Galina M. Yakovleva
(74) *Attorney, Agent, or Firm* — Gavrilovich, Dodd & Lindsey LLP

(57) ABSTRACT

Components for enabling immunodection of indazole synthetic cannabinoids are described including immunogens, haptens, antibodies, methods and kits.

9 Claims, 6 Drawing Sheets

DETECTION OF INDAZOLE SYNTHETIC CANNABINOIDS

RELATED APPLICATIONS

Figure 1:
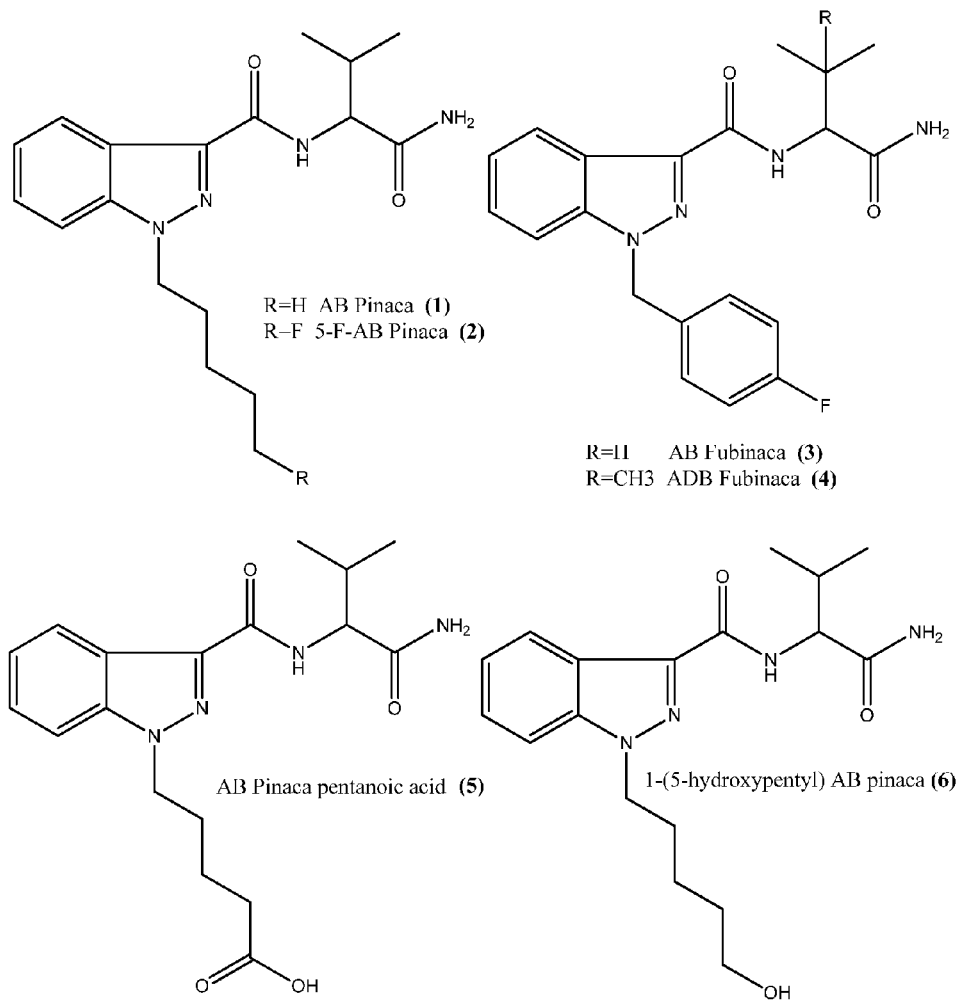
Figure 1:
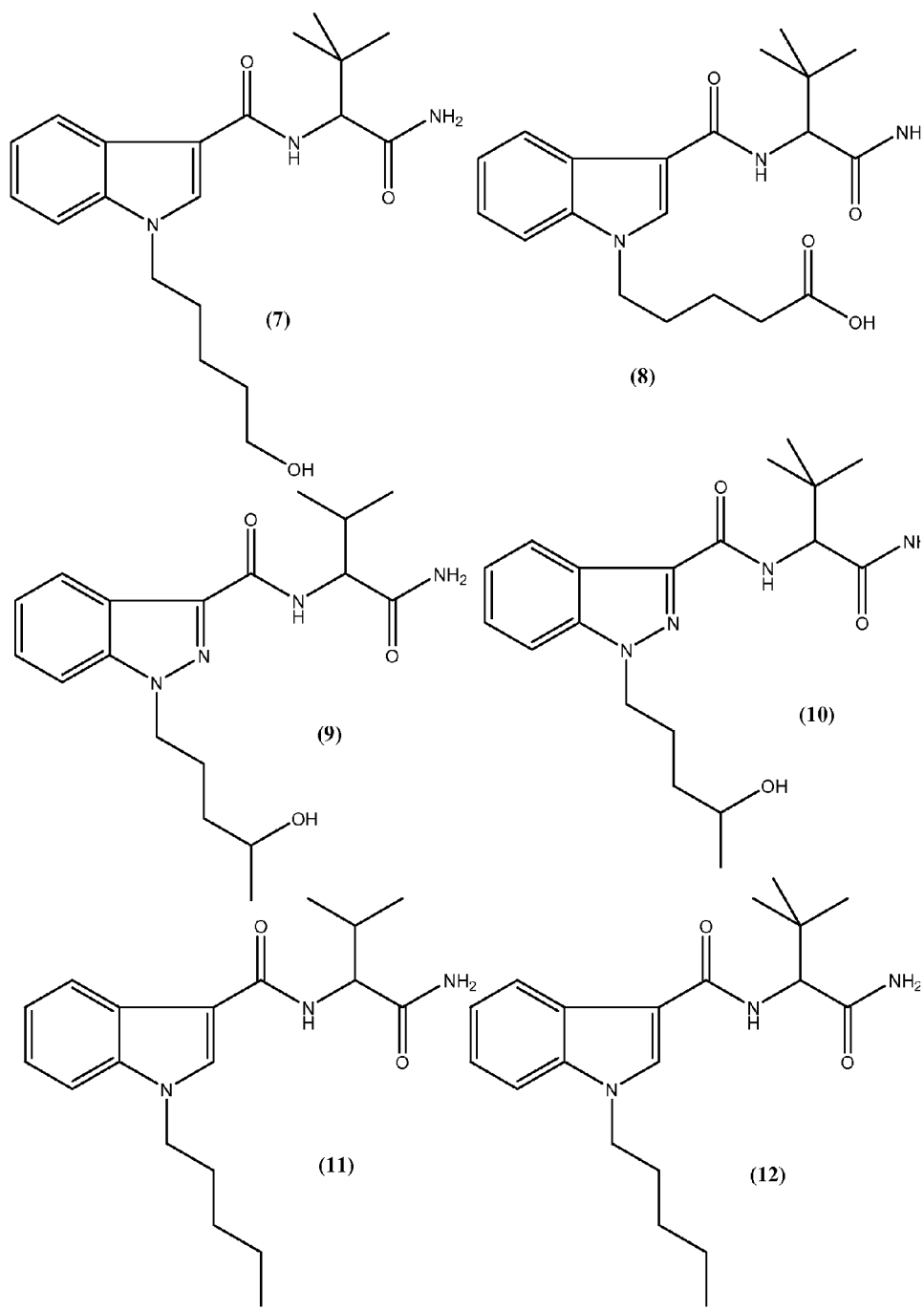
Figure 1:
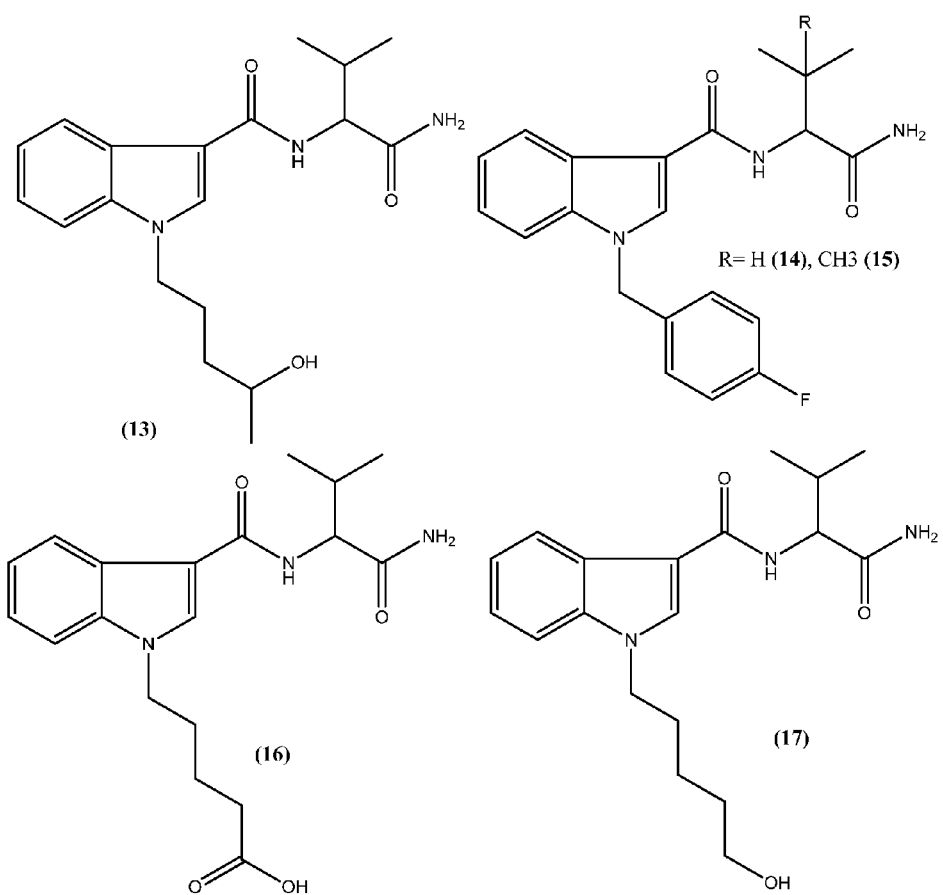
Figure 1:
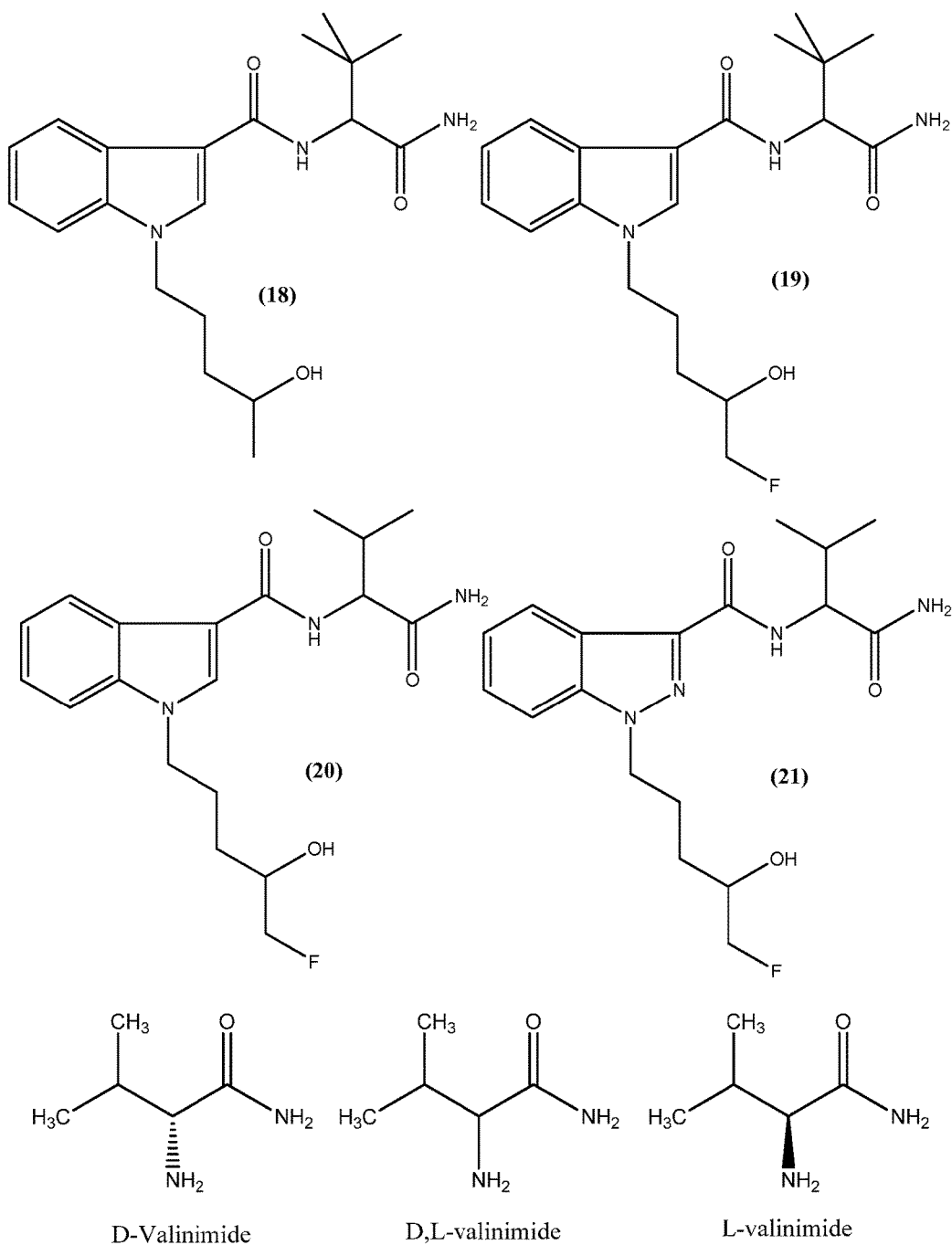

The instant application claims the benefit of priority under 35 USC § 119 to United Kingdom Application No. 1416624.3, entitled "Detection of indazole synthetic cannabinoids" filed Sep. 19, 2014 and to United Kingdom Application No. 1416733.2, entitled "Detection of indazole synthetic cannabinoids" filed Sep. 22, 2014, the entire contents of each of which are incorporated herein by reference in their entirety.

BACKGROUND

Synthetic cannabinoids (SCs) represent a major problem to society and their use is increasing. Synthetic cannabinoids have been marketed under the guise of "herbal incense," and promoted by drug traffickers as legal alternatives to marijuana. Newer generations of synthetic cannabinoid substances are continually emerging in the U.S. illicit drug market.

N-(1-amino-3-methyl-1-oxobutan-2-yl)-1-pentyl-1H-indazole-3-carboxamide, also known as AB-PINACA, is one such new-generation synthetic cannabinoid receptor agonist (SCRA). It has a core indazole structure and a carboxamide linkage. AB-PINACA was first identified as a component of synthetic cannabis products in Japan in 2012. It is similar in structure to the other new generation synthetic cannabinoids ADB-FUBINACA (N-(1-amino-3,3-dimethyl-1-oxobutan-2-yl)-1-(4-fluorobenzyl)-1H-indazole-3-carboxamide) and AB-FUBINACA (N-(1-amino-3-methyl-1-oxobutan-2-yl)-1-(4-fluorobenzyl)-1H-indazole-3-carboxamide). According to Drugs Forum website dosage is in the region of 2-15 mg.

The most common route of administration is via smoking, but the drug can also be taken orally and by inhalation. AB-PINACA is most frequently found as a component of herbal mixtures/blends suitable for smoking. AB-PINACA is described by users on the Drugs Forum website as 'a stronger version of JWH-018' and 'twice as strong as the last batch of synthetic cannabinoids'. It is said to produce a 'dreamy high' and is said to be 'very sedating . . . opium-like'. 5-Fluoro-AB-PINACA is considered 'super-stimulatory' and 'way more potent than normal AB-PINACA'.

In 2013 AB-PINACA (and ADB-FUBINACA) was classed as a "Designated Substance" under the Pharmaceutical Affairs Law in Japan. AB-PINACA is a Schedule I drug in the USA. AB-PINACA has been scheduled in Victoria, Australia (2013). Structurally related AB-FUBINACA was temporarily made a Schedule I drug in the US in January 2014 due to imminent threat to public health.

The defining feature of the Pinaca family (See FIG. 1 for members and metabolites) is a 3-amido-indazole structure with a 1-N substituent and a N-amide substituent consisting of either 1-amino-1-carbonyl-3-methylbut-2-yl (Z=H) or 1-amino-1-carbonyl-3,3-dimethylbut-2-yl (Z=CH₃) i.e.:

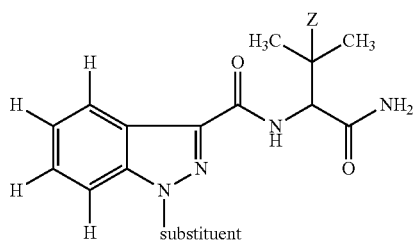

Structure A in which Z is H or $CH_3$ and substituent may be selected from, but is not limited to, pentanoic acid, 5-fluoropentyl, 5-hydroxylpentyl, 4-hydroxylpentyl, pentyl, 5-fluoro-4-hydroxylpentyl; and (4-fluoro-phenyl)methyl.

Substituents off an indazole are numbered as follows:

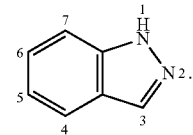

Detection of this family and their key metabolites is necessary for toxicological screening and drug identification. Mass-spectrometry (MS) detection of Pinaca family members has been described (Takayama 2014). MS detection, however, is time consuming and requires expensive equipment as well as highly trained operators. A need exists for rapid detection of SC's Pinaca family.

SUMMARY OF THE INVENTION

Described is the first known immunoassay for the selective detection and determination of synthetic cannabinoids of the Pinaca family. The immunoassay is underpinned by novel and sensitive antibodies able to detect Pinaca family derivatives whose substituents vary at both the 1- and 3-positions of the indazole ring. The invention further describes substrates comprising an antibody to compounds of the Pinaca family. Also described are novel immunogens, haptens, hapten synthetic methods, methods and kits incorporating antibodies of the invention.

In one embodiment, the invention is an immunogen of structure I:

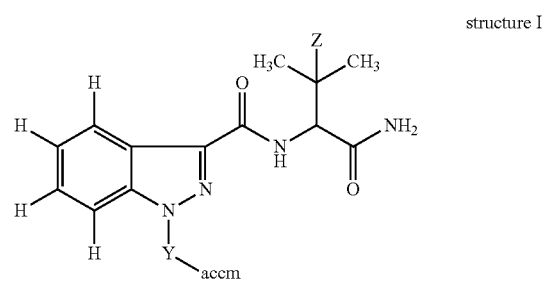

structure I wherein: Z is H or $CH_3$; Y is a crosslinking group; and accm is an antigenicity-conferring carrier material. In one embodiment, Y is -(A)$_n$-B-D-; A is a functional group or heteroatom enabling attachment of the crosslinking group to the indazole; B is a $C_{1-10}$ substituted or unsubstituted alkylene moiety optionally incorporating an aryl, cycloalkyl and/or a heterocyclic moiety; D is a functional group or heteroatom enabling attachment of the crosslinking group to the antigenicity-conferring carrier material; and n=0 or 1. In another embodiment, n=0; and D is —C(O)—, —NH—, —C≡, —C(O)—NH—, —C(O)—NH—CH(COOH)—CH₂—CH₂—S—, —C(O)—NH—CH(COOH)—CH₂—CH₂—S-maleimide- or —S—.

In yet another embodiment, the invention is a hapten of structure II:

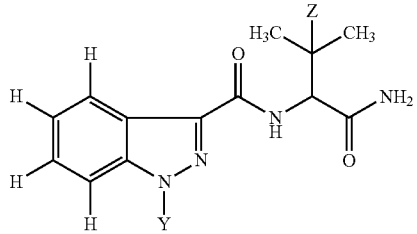

structure II wherein: Z is H or CH$_3$; Y is -(A)$_n$-B-D; A is attached to the indazole and is, optionally, —C(O)— or —C(O)—O—; B is a C$_{1-10}$ substituted or unsubstituted alkylene moiety optionally incorporating an aryl, cycloalkyl and/or a heterocyclic moiety; D is a functional group; and n=0 or 1. In one embodiment, B is a C$_{1-10}$ substituted or unsubstituted alkylene moiety optionally incorporating an aryl moiety; D is —CHO, —NH$_2$, —CO$_2$H, —CO$_2$Me, —CO$_2$Et, —CO$_2$Pr, —CO$_2$isoPr, —CO$_2$But, —CO$_2$isoBut, —CO$_2$tertBut, —OH, —C(O)—NH-4-butyrothiolactone, —C(O)—NH—CH(COOH)—CH$_2$—CH$_2$—SH, —C(O)—NH—CH(COOH)—CH$_2$—CH$_2$—S-maleimide or —SH; and n=0.

In another embodiment, the invention is a method of synthesising a hapten of structure II, wherein: B is a C$_{1-6}$ substituted or unsubstituted alkylene moiety optionally incorporating an aryl moiety; and D is —CO$_2$Me, —CO$_2$Et, —CO$_2$Pr, —CO$_2$isoPr, —CO$_2$But, —CO$_2$isoBut or —CO$_2$tertBut; and n=0; comprising the steps of: i) alkylating 3-carboxyindazole by reaction with a terminally halogenated alkylene ester in which the alkylene moiety is C$_{1-6}$ and the ester moiety is —CO$_2$Me, —CO$_2$Et, —CO$_2$Pr, —CO$_2$isoPr, —CO$_2$But, —CO$_2$isoBut or —CO$_2$tertBut; and ii) contacting the product of i) with valinimide.

In yet another embodiment, the present invention is an antibody which binds to an epitope of structure IIIb:

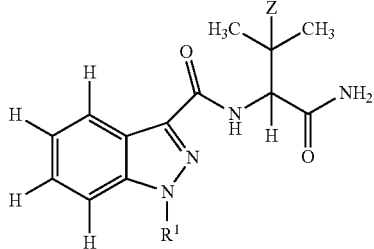

structure IIIb wherein: Z is H or CH$_3$; and R$^1$ is a substituted or unsubstituted C$_{1-10}$ alkyl moiety optionally incorporating an aryl, cycloalkyl and/or a heterocyclic moiety; further optionally, R$^1$ is pentanoic acid, 5-fluoropentyl, 5-hydroxylpentyl, 4-hydroxylpentyl, pentyl, 5-fluoro-4-hydroxylpentyl, or (4-fluoro-phenyl)methyl. In one embodiment, the antibody is raisable from an immunogen of structure I. In one embodiment, the antibody has a cross-reactivity of 100% to AB-Pinaca Pentanoic acid and greater than 50% cross-reactivity to AB-Pinaca, 1-(5-hydroxypentyl) AB-Pinaca, 1-(4-hydroxypentyl) AB-Pinaca, and 5-fluoropentyl AB-Pinaca; a cross-reactivity of 100% to AB-Pinaca Pentanoic acid and greater than 75% cross-reactivity to 1-(5-hydroxypentyl) AB-Pinaca, 1-(4-hydroxypentyl) AB-Pinaca, and 5-fluoropentyl AB-Pinaca; or a cross-reactivity of 100% to AB-Pinaca Pentanoic acid and greater than 50% cross-reactivity to AB-Pinaca, 1-(5-hydroxypentyl) AB-Pinaca, 1-(4-hydroxypentyl) AB-Pinaca, and 5-fluoropentyl AB-Pinaca and less than 50% to AB-Fubinaca. In another embodiment, the antibody has an IC$_{50}$ of less than about 20 ng/ml to AB-Pinaca, 1-(5-hydroxypentyl) AB-Pinaca, 5-fluoropentyl AB-Pinaca, AB-Pinaca Pentanoic acid, and AB-Fubinaca.

In another embodiment, the invention is a method of detecting or determining a compound comprising structure IIIb:

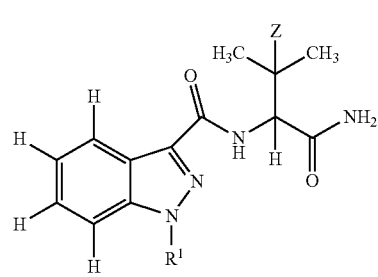

structure IIIb wherein: Z is H or CH$_3$; and R$^1$ is a substituted or unsubstituted C$_{1-10}$ alkyl moiety optionally incorporating an aryl, cycloalkyl and/or a heterocyclic moiety; further optionally, R$^1$ is pentanoic acid, 5-fluoropentyl, 5-hydroxylpentyl, 4-hydroxylpentyl, pentyl, 5-fluoro-4-hydroxylpentyl, or (4-fluoro-phenyl)methyl; in an in vitro sample or in a solution comprising: i. contacting the sample or solution with a detecting agent and an antibody of the invention, wherein both the compound and the detecting agent bind to the antibody; and ii. Detecting or determining the amount of detecting agent bound to the antibody. In one embodiment, the compound of structure IIIb is one or more of AB-Pinaca, 1-(5-hydroxypentyl) AB-Pinaca, 1-(4-hydroxypentyl) AB-Pinaca, and 5-fluoropentyl AB-Pinaca; or one or more of AB-Pinaca, AB-Pinaca pentanoic acid, 1-(5-hydroxypentyl) AB-Pinaca, 1-(4-hydroxypentyl) AB-Pinaca, and 5-fluoropentyl AB-Pinaca.

In yet another embodiment, the invention is a detecting agent comprising:

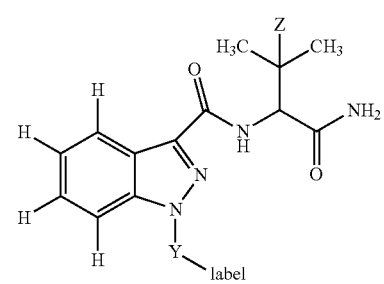

structure IV wherein: Z is H or CH$_3$; Y is a crosslinking group; and label is an labelling agent. In one embodiment, Y is -(A)$_n$-B-D-; A is a functional group or heteroatom enabling attachment of the crosslinking group to the indazole; B is a C$_{1-10}$ substituted or unsubstituted alkylene moiety optionally incorporating an aryl, cycloalkyl and/or a heterocyclic moiety; D is a functional group or heteroatom enabling attachment of the crosslinking group to the labelling agent; and n=0 or 1. In another embodiment, n=0; and D is —C(O)—, —NH—, —C≡, —C(O)—NH—, —C(O)—NH—CH(COOH)—CH₂—CH₂—S—, —C(O)—NH—CH(COOH)—CH₂—CH₂—S-maleimide- or —S—.

In one embodiment, the invention is a kit comprising an antibody described herein.

REFERENCES

Takayama et al (2014). UPLC/ESI-MS/MS-based determination of metabolism of several new illicit drugs, ADB-Fubinaca, AB-Fubinaca, AB-Pinaca, Qupic, 5F-Qupic and alpha-PVT, by human liver microsome. *Biomed. Chromatogr,* 28: 831-838.

FIGURES

FIG. 1, Structures of Pinaca Derivatives and valinimide.

Figure 2:
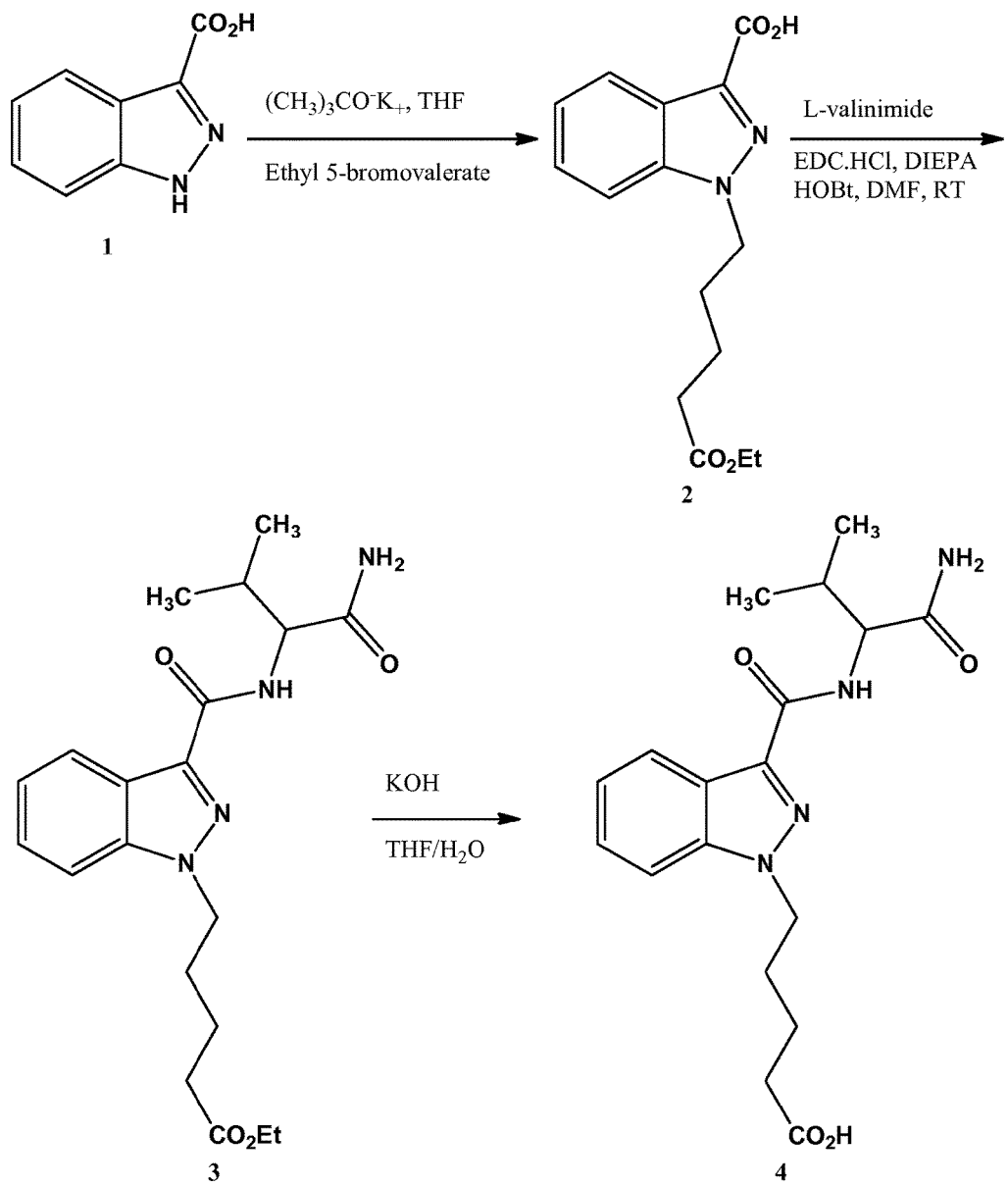

FIG. 2, Exemplary schematic showing synthesis of Pinaca derivative (AB-Pinaca pentanoic acid).

Figure 3:
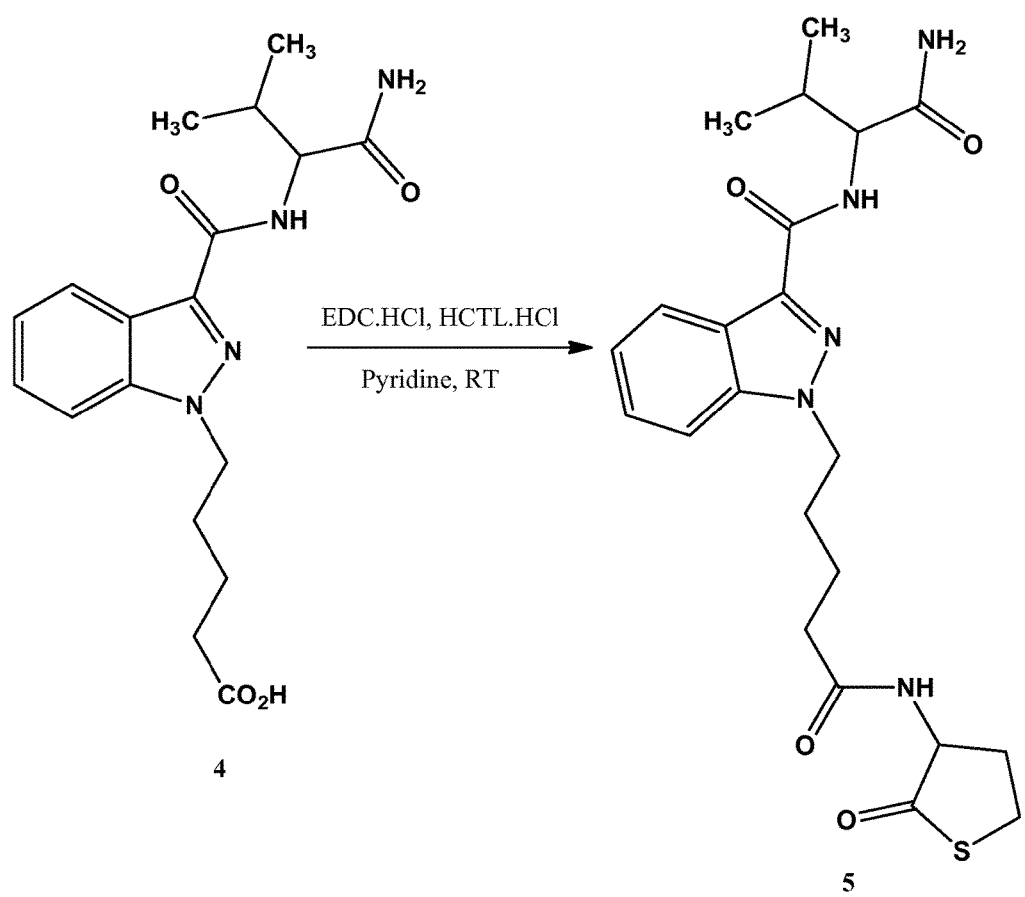

FIG. 3, Exemplary schematic showing Pinaca hapten synthesis.

DETAILED DESCRIPTION OF THE INVENTION

In a first aspect, the invention describes an immunogen of structure I:

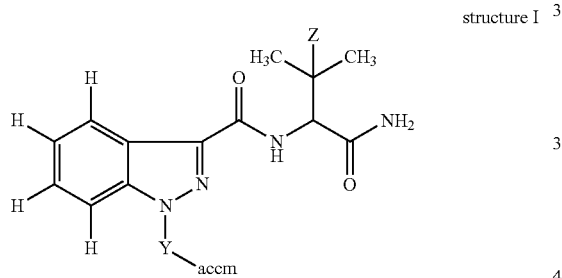

structure I in which Z is H or CH₃; Y is a crosslinking group and accm is an antigenicity-conferring carrier material. Numerous crosslinkers and accms are commercially available and have been described in the literature (Thermo Scientific Crosslinking Technical Handbook, 1606073 April 2009; Bioconjugate Techniques G. Hermanson, ed, Academic Press, 1996, 785 pp—lists common carrier proteins). An example of a crosslinking group is 4-N-maleimidomethylcyclohexyl-1-carboxylic acid NHS ester solution (available from Sigma-Aldrich). An alternative crosslinker which can be used to couple to haptens possessing a carboxylic acid is EDC and either sulfo-NHS (N-hydroxysulfosuccinimide) or homocysteinethiolactone, all of which are known in the art and are commercially available.

In a preferred embodiment, Y is -(A)$_n$-B-D- in which B is a $C_{1-10}$ substituted or unsubstituted, a $C_{1-6}$ substituted or unsubstituted, or a $C_4$ substituted or unsubstituted alkylene moiety optionally incorporating (i.e., wherein a methylene group of the alkylene is replaced) an aryl, cycloalkyl and/or a heterocyclic moiety; n=0 or 1; and A is a functional group or heteroatom enabling attachment of the crosslinker to the N-atom of the indazole and D is a functional group or heteroatom enabling attachment of the crosslinker to the antigenicity-conferring carrier material.

In a preferred embodiment, Y is -(A)$_n$-B-D- in which B is a $C_{1-10}$ substituted or unsubstituted, preferably a $C_{1-6}$ substituted or unsubstituted, or in one embodiment a $C_4$ substituted or unsubstituted alkylene moiety optionally incorporating a cycloalkyl and/or a heterocyclic moiety; n=0 or 1; and A is a functional group or heteroatom enabling attachment of the crosslinker to the N-atom of the heterocycle (i.e., indazole) and D is a functional group or heteroatom enabling attachment of the crosslinker to the antigenicity-conferring carrier material.

In one embodiment, B is substituted with halogen, haloalkyl, —OH, —C(O)₂H, —C(O)₂Me, —C(O)₂Et, or —NH₂. In one embodiment, B is substituted with F, CH₂F, —OH, —C(O)₂H, —C(O)₂Me, or —C(O)₂Et. The term "functional group" is a standard phrase in the chemistry field and refers to a reactive group such as an amine, ketone, ether, thioether, amide, alkene, thiol, ester, carboxylic acid or aldehyde.

In one embodiment, the immunogen of structure I has n=0; or, if n=1, the functional group or heteroatom A of Y can be —C(O)— or —C(O)—O—. The functional group or heteroatom D of Y is —C(O)—, —NH—, —C≡, —C(O)—NH—, —C(O)—NH—CH(COOH)—CH₂—CH₂—S—, —C(O)—NH—CH(COOH)—CH₂—CH₂—S-maleimide- or —S—. Preferably, the immunogen of structure I has n=0; and the functional group or heteroatom D of Y is —C(O)—, —NH—, —C(O)—NH—, —C≡, or —S—. For the avoidance of doubt in, for example, the formation of a tracer from Hapten-2: the KOH solution opens the ring structure below at the thioamide bond and the free —SH group thus formed attaches to maleimide-HRP, i.e. forming indazole-(CH₂)₄—C(O)—NH—CH(COOH)—CH₂—CH₂—S-maleimide-HRP, so that D is —C(O)—NH—CH(COOH)—CH₂—CH₂—S—. Typical accms for attachment to the crosslinker are keyhole limpet haemocyanin (KLH), bovine thyroglobulin (BTG), bovine serum albumin (BSA), egg ovalbumin, bovine gamma globulin or cationised BSA.

A second aspect of the invention is a compound of structure II:

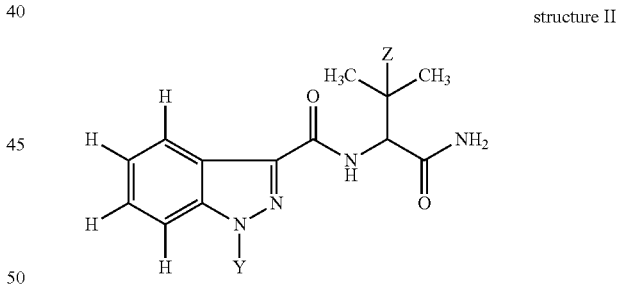

structure II in which Z is H or CH₃; Y is -(A)$_n$-B-D in which n=0 or 1, A is attached to the N-atom of the indazole and is —C(O)— or —C(O)—O—; B is a $C_{1-10}$ substituted or unsubstituted, a $C_{1-6}$ substituted or unsubstituted, or a $C_4$ substituted or unsubstituted alkylene moiety optionally incorporating an aryl, cycloalkyl and/or a heterocyclic moiety; preferably and aryl moiety; and D is a functional group. D can be —CHO, —NH₂, —CO₂H, —CO₂Me, —CO₂Et, —CO₂Pr, —CO₂isoPr, —CO₂But, —CO₂isoBut, —CO₂tertBut, —OH, —C(O)—NH-4-butyrothiolactone, or —SH; or be —CHO, —NH₂, —CO₂H, —CO₂Me, —CO₂Et, —CO₂Pr, —CO₂isoPr, —CO₂But, —CO₂isoBut, —CO₂tertBut, —OH, —C(O)—HCTL, —C(O)—NH—CH(COOH)—CH₂—CH₂—SH, —C(O)—NH—CH(COOH)—CH₂—CH₂—S-maleimide or —SH. In another embodiment, Z is H or CH₃; Y is -(A)$_n$-B-D; A is attached to the N-atom of the indazole and is —C(O)— or —C(O)—O—; B is a $C_{1-10}$ substituted or unsubstituted alkylene moiety optionally incorporating an aryl, cycloalkyl and/or a heterocyclic moiety; D is a functional group; and n=0 or 1; preferably: B is a $C_{1-10}$ substituted or unsubstituted alkylene moiety optionally incorporating an aryl moiety; D is —CHO, —$NH_2$, —$CO_2H$, —$CO_2Me$, —$CO_2Et$, —$CO_2Pr$, —$CO_2isoPr$, —$CO_2But$, —$CO_2isoBut$, —$CO_2tertBut$, —OH, —C(O)—NH-4-butyrothiolactone, or —SH, OR D is —CHO, —$NH_2$, —$CO_2H$, —$CO_2Me$, —$CO_2Et$, —$CO_2Pr$, —$CO_2isoPr$, —$CO_2But$, —$CO_2isoBut$, —$CO_2tertBut$, —OH, —C(O)—HCTL, —C(O)—NH—CH(COOH)—$CH_2$—$CH_2$—SH, —C(O)—NH—CH(COOH)—$CH_2$—$CH_2$—S-maleimide or —SH; and n=0.

Compounds of structure II are useful as haptens and can be linked with accm to form immunogens of the invention.

In another embodiment, Z is H or $CH_3$; Y is -(A)$_n$-B-D in which n=0 or 1, A is attached to the N-atom of the heterocycle (i.e., indazole) and is —C(O)— or —C(O)—O—; B is a $C_{1-10}$ substituted or unsubstituted, preferably a $C_{1-6}$ substituted or unsubstituted, or in one embodiment, a $C_3$ or $C_4$ substituted or unsubstituted alkylene moiety optionally incorporating a cycloalkyl and/or a heterocyclic moiety; and D is a functional group. D is preferably —CHO, —$NH_2$, —$CO_2H$, —$CO_2Me$, —$CO_2Et$, —$CO_2Pr$, —$CO_2isoPr$, —$CO_2But$, —$CO_2isoBut$, —$CO_2tertBut$ or —SH; or more preferably D is —$CO_2Me$, —$CO_2Et$, —$CO_2Pr$, —$CO_2isoPr$, —$CO_2But$, —$CO_2isoBut$, or —$CO_2tertBut$. Preferably n=0.

In one embodiment, B is substituted with halogen, haloalkyl, —OH, —C(O)$_2$H, —C(O)$_2$Me, —C(O)$_2$Et, or —$NH_2$. In one embodiment, B is substituted with F, $CH_2F$, —OH, —C(O)$_2$H, —C(O)$_2$Me, or —C(O)$_2$Et.

The compound of structure II is also referred to as a hapten. It is preferable to acquire a hapten commercially to avoid difficult and resource intensive syntheses. Haptens of structure II were not commercially available and were thus synthesised in-house.

The term "hapten" as used herein describes a pre-immunogenic molecule that stimulates antibody production only when linked to a larger carrier molecule. For the purposes of this patent application, "linked" is synonymous with bound, attached, conjugated, crosslinked, coupled, or chemically synthesised to. This larger carrier molecule can be referred to as an antigenicity-conferring carrier material (accm). Once the hapten is linked to the accm, it forms the immunogen.

The term "immunogen" as used herein, describes an entity that induces an immune response such as production of antibodies or a T-cell response in a host animal.

The term "carrier molecule" refers to a molecule to which a hapten or antigen can be linked to impart immunogenic properties to the hapten or antigen. The term "carrier molecule" may be used interchangeably with the terms "carrier", "immunogenicity conferring carrier molecule" and "antigenicity conferring carrier material".

The accm can be any material that makes all or part of the hapten susceptible to antibody recognition and binding. For example, the accm can be a protein, a protein fragment, a synthetic polypeptide or a semi-synthetic polypeptide. Alternatively, the accm comprises synthetic poly (amino acids) having a sufficient number of available amino groups, such as lysine. Further alternatively, the accm is selected from synthetic or natural polymeric materials bearing reactive functional groups. Still further alternatively, the accm is selected from carbohydrates, yeasts and polysaccharides. Illustrative examples of useful antigenicity-conferring carrier materials are bovine serum albumin (BSA), egg ovalbumin (OVA), bovine gamma globulin (BGG), bovine thyroglobulin (BTG), keyhole limpet haemocyanin (KLH) etc. Optionally the accm is selected from KLH or BSA.

It will be understood that the haptens of the current invention may be attached to the antigenicity-conferring carrier material (accm) via a crosslinking group. The crosslinking group may be any conventional cross linking group conventionally used in this field. The crosslinking group is ideally a functionalised linking group joining the accm to the hapten. The term "crosslinking group" as used herein is any bifunctional molecule able to covalently join the hapten element to an immunogenicity conferring carrier material. A suitable crosslinking group to link with alternative carrier materials is maleimide, or a maleimide derivative, for example when BTG-maleimide is used to conjugate with the hapten via a cysteine residue. Other cross-linking groups which could also couple this group on the cysteine include haloacetyls and pyridyldisulfides. Either Lys residue, or the Glu residue (C-terminal) may alternatively be used to conjugate to a carrier material, optionally via a cross-linking group, to form an immunogen. For example, a primary amine group on the side chain of lysine (Lys) could be coupled using a crosslinking group selected from N-hydroxysuccinimide esters, imidoesters, PFP esters or hydroxymethyl phosphine. As another example, glutamic acid (Glu) could be coupled using a carbodiimide crosslinking group: 1-Ethyl-3-(3-dimethylaminopropyl)carbodiimide EDC or N,N'-Dicyclohexylcarbodiimide (DCC). In one embodiment, the cross-linking group may comprise or consist of a carboxyl, dithiopyridyl, maleimidyl, amino, hydroxyl, thiol and aldehyde moiety. The cross-linking group is well known to the skilled person in immunogen synthesis. As described herein, compounds of the invention may optionally be substituted with one or more substituents, such as illustrated generally below, or as exemplified by particular species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list.

Selection of substituents and combinations of substituents envisioned by this invention are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The term "alkyl" as used herein means a saturated straight or branched chain hydrocarbon.

The term "alkylene," as used herein, represents a saturated divalent straight or branched chain hydrocarbon group and is exemplified by methylene, ethylene, isopropylene and the like.

The term "cycloalkyl" (or "carbocycle") refers to a monocyclic, bicyclic or polycyclic fused, spiro or bridged cyclic ring (typically a monocyclic $C_3$-$C_8$ hydrocarbon or bicyclic $C_8$-$C_{12}$ hydrocarbon) that is completely saturated and has a single point of attachment to the rest of the molecule, and wherein any individual ring in said bicyclic ring system has 3-8 members. Suitable cycloalkyl groups include, but are not limited to, cyclopropyl, cyclobutyl, cyclopentyl, cyclohexyl, and cycloheptyl.

The term "heterocycle" (or "heterocyclyl", or "heterocyclic" or "non-aromatic heterocycle") as used herein refers to a non-aromatic ring system which can be saturated or contain one or more units of unsaturation, having three to fourteen ring atoms in which one or more ring carbons is replaced by a heteroatom such as, N, S, or O and each ring in the system contains 3 to 8 members. In some embodiments, non-aromatic heterocyclic rings comprise up to three heteroatoms selected from N, S and O within the ring. In other embodiments, non-aromatic heterocyclic rings comprise up to two heteroatoms selected from N, S and O within the ring system. In yet other embodiments, non-aromatic heterocyclic rings comprise up to two heteroatoms selected from N and O within the ring system. The term includes monocyclic, bicyclic or polycyclic fused, spiro or bridged heterocyclic ring systems. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, 3-(1-alkyl)-benzimidazol-2-onyl, and 1,3-dihydro-imidazol-2-onyl.

The term "aryl" (or "aryl ring" or "aryl group") used alone or as part of a larger moiety as in "aralkyl", "aralkoxy", "aryloxyalkyl", or "heteroaryl" refers to both carbocyclic or heterocyclic aromatic ring systems. The term "aryl" may be used interchangeably with the terms "aryl ring" or "aryl group".

"Carbocyclic aromatic ring" groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring" or "carbocyclic aromatic", as it is used herein, is a group in which an aromatic ring is "fused" to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The terms "heteroaryl", "heteroaromatic", "heteroaryl ring", "heteroaryl group", "aromatic heterocycle" or "heteroaromatic group", used alone or as part of a larger moiety as in "heteroaralkyl" or "heteroarylalkoxy", refer to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Also included within the scope of the term "heteroaryl", as it is used herein, is a group in which an aromatic ring is "fused" to one or more non-aromatic rings (carbocyclic or heterocyclic), where the radical or point of attachment is on the aromatic ring. Bicyclic 6.5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "heteroatom" means one or more of oxygen, sulphur, nitrogen, or phosphorus, including any oxidized form of nitrogen, sulphur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR+ (as in N-substituted pyrrolidinyl).

The term "unsaturated," as used herein, means that a moiety has one or more units of unsaturation.

The terms "γ-thiobutyrolactone" and "4-butyrothiolactone" as used herein refers to: γ-

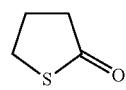

The "2-amino-4-mercaptobutyric acid 1,4-thiolactone", and "homocysteine thiolactone (HCTL)" and as used herein refer to:

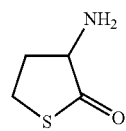

Suitable substituents on a saturated or unsaturated carbon of an alkyl, aryl, cycloalkyl, or heterocyclic ring are $C_1$-$C_6$ alkyl, halogen, cyano, oxo, —NCO, —$OR^b$, —$SR^b$, —S(O)$R^a$, —$SO_2Ra$, —$NR^bR^c$, —C(O)$R^b$, —C(O)$OR^b$, —OC(O)$R^b$, —NRC(O)$R^b$, —C(O)$NR^bR^c$, —$NR^bC(O)NR^bR^c$, —$NR^bC(O)OR^b$, —$OCONR^bR^c$, —C(O)$NRCO_2R^b$, —$NR^bC(O)NR^cC(O)OR^b$, —C(O)NR(O$R^b$), —$SO_2NR^cR^b$, —$NR^bSO_2R^b$, —$NR^bSO_2NR^cR^b$, or —P(O)($OR^a$)$_2$—; or two substituents join together with the atoms to which they are attached to form a 5-7-membered cycloalkyl or heterocyclic ring.

Each $R^a$, $R^b$ and $R^c$ are each independently —H or $C_1$-$C_6$ alkyl.

Other suitable substituents for a saturated carbon of an alkyl, carbocyclic or heterocyclic ring include the following: =O, =S, =NNHR*, =NN(R*)$_2$, =NNHC(O)R*, =NNHCO$_2$(alkyl), =NNHSO$_2$(alkyl), or =NR*, wherein each R* is independently selected from —H or $C_1$-$C_6$ alkyl.

In some embodiments, suitable substituents on the nitrogen of a heteroaryl or heterocyclic ring include those listed above for carbon atoms. Other suitable substituents include —$R^+$, —N($R_+$)$_2$, —C(O)$R^+$, —$CO_2R^+$, —C(O)C(O)$R^+$, —C(O)CH$_2$C(O)$R^+$, —$SO_2R^+$, —$SO_2N(R^+)_2$, —C(=S)N($R^+$)$_2$, —C(=NH)—N($R^+$)$_2$, or —$NR^+SO_2R^+$; wherein $R^+$ is —H or $C_1$-$C_6$ alkyl.

Nitrogen containing rings that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Nitrogen containing rings such as pyrazinyl that are substituted on a ring nitrogen and attached to the remainder of the molecule at a second ring nitrogen atom are said to be N' substituted-N-heterocycles. For example, an N' acyl N-pyrazinyl group is attached to the remainder of the molecule at one ring nitrogen atom and substituted at the second ring nitrogen atom with an acyl group.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this invention, unless only one of the isomers is drawn specifically. As would be understood to one skilled in the art, a substituent can freely rotate around any rotatable bonds. Therefore, single stereochemical isomers as well as enantiomeric, diastereomeric, cis/trans, conformational, and rotational mixtures of the present compounds are within the scope of the invention. Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. Such compounds, especially deuterium analogues, can also be therapeutically useful.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The invention further describes a method of synthesising a compound of structure II in which n=0, B is $C_{1-6}$ substituted or unsubstituted alkylene moiety optionally incorporating an aryl moiety and D is —$CO_2Me$, —$CO_2Et$, —$CO_2Pr$, —$CO_2isoPr$, —$CO_2But$, —$CO_2isoBut$, —$CO_2tertBut$; or n=0, B is $C_{1-6}$ alkylene moiety and D is —$CO_2Me$, —$CO_2Et$, —$CO_2Pr$, —$CO_2isoPr$, —$CO_2But$, —$CO_2isoBut$, —$CO_2tertBut$ comprising:

i) alkylating 3-carboxyindazole by reaction with a terminally halogenated alkylene ester in which the alkyene moiety is $C_{1-6}$ and the ester moiety is —$CO_2Me$, —$CO_2Et$, —$CO_2Pr$, —$CO_2isoPr$, —$CO_2But$, —$CO_2isoBut$ or —$CO_2tertBut$, and ii) contacting or reacting the product of i) with valinimide.

The method can incorporate a further step in which the ester group is hydrolysed so that an acid is formed.

The synthetic method can be effected using L-valinimide, D-valinimide or a mixture of the two enantiomers (D,L-valinimide). The immunogen of the invention is also amenable to derivation based on a specific enantiomer or a mixture of the two enantiomers of valinimide. An example of this synthetic method is provided in the General Methods, Example and Results section and a schematic is provided in FIG. 2. The skilled synthetic chemist is aware that the described experimental conditions in the Examples section are amenable to a degree of flexibility without affecting the nature of the end product.

In another embodiment, the invention describes a method of synthesising a compound of Structure II in which D is —$CO_2Me$, —$CO_2Et$, —$CO_2Pr$, —$CO_2isoPr$, —$CO_2But$, —$CO_2isoBut$, —$CO_2tertBut$ comprising:

i) alkylating 3-carboxyindazole with a terminally halogenated alkylene ester in which the alkyene moiety is $C_{1-6}$ and the ester moiety is —$CO_2Me$, —$CO_2Et$, —$CO_2Pr$, —$CO_2isoPr$, —$CO_2But$, —$CO_2isoBut$ or —$CO_2tertBut$, and ii) contacting or reacting the product of i) with valinimide.

As used herein, the terms "contacting", "reacting" or "reaction" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. It is also understood that the indicated and/or desired product may be produced in any amount greater than 1%, for example, more than about 5%, more than about 15%, more than about 50%, more than about 75% more than about 80% more than about 90% more than about 95% or 100%.

The invention further describes an antibody which binds or specifically binds to an epitope of structure IIIa or IIIb, in which Z is H or $CH_3$ and the N1 of the indazole is substituted with $R^1$, wherein $R^1$ is a $C_{1-10}$ substituted or unsubstituted, or $C_{1-5}$ substituted or unsubstituted alkyl moiety optionally incorporating an aryl, cycloalkyl and/or heterocyclic moiety; or the N1 of the indazole is optionally substituted with $R^1$, wherein $R^1$ is pentanoic acid, 5-fluoropentyl, 5-hydroxylpentyl, 4-hydroxylpentyl, pentyl, 5-fluoro-4-hydroxylpentyl; and (4-fluoro-phenyl)methyl.

In structure IIIa, non-specified valencies, specifically at the 2-position of 3-methylbut-2-yl (Z=H)/3,3-dimethylbut-2-yl(Z=CH₃); and at N-1 of the indazole are deliberate and indicate that the antibody can bind to an epitope in which a wide variety of substitutions at these positions can be tolerated without affecting the ability of the antibody to bind thereto. In structure IIIb, all valencies have been specified.

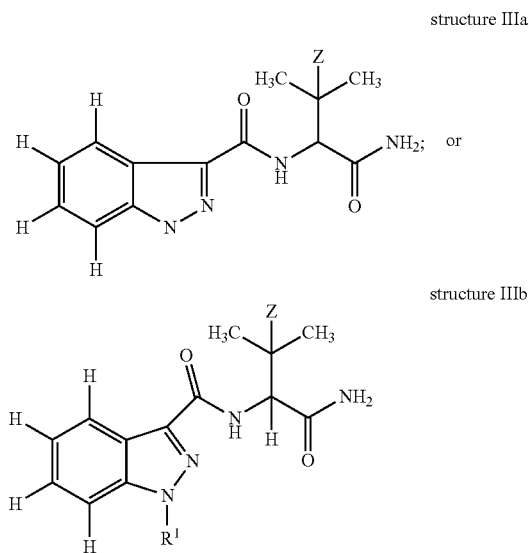

structure IIIa structure IIIb

In one embodiment, of structure IIIa, H is present as the final valency at the 2-position of 3-methylbut-2-yl (Z=H)/3,3-dimethylbut-2-yl (Z=CH₃); and N-1 of the indazole is substituted with pentanoic acid, 5-fluoropentyl, 5-hydroxylpentyl, 4-hydroxylpentyl, pentyl, 5-fluoro-4-hydroxylpentyl, pentanoic acid HCTL or (4-fluoro-phenyl)methyl.

In one embodiment, of structure IIIb, $R^1$ is pentanoic acid, 5-fluoropentyl, 5-hydroxylpentyl, 4-hydroxylpentyl, pentyl, 5-fluoro-4-hydroxylpentyl, pentanoic acid HCTL or (4-fluoro-phenyl)methyl.

As discussed below, the antibody can bind to part of or the whole structure, or a structure which comprises structure IIIa or IIIb above. The antibody is derived from an immunogen of the invention. The phrase 'an antibody which binds or specifically binds to an epitope of structure . . . ' implies that the antibody, if polyclonal, will comprise clones whose high concentration and binding characteristics ensure an assay incorporating the antibody will bind to and ultimately support the identification of Pinaca molecules incorporating structure IIIa or IIIb. Alternatively, the antibody could be a monoclonal antibody specific for a particular structural part of or the whole of structure IIIa or IIIb. There are several parameters that can be used to compare the relative degree of binding to an antibody of different analytes including the lowest limit of detection, the lowest limit of quantification and the $IC_{50}$. The $IC_{50}$ is determined using a competitive assay (see Example 9 of the General Method, Examples and Results and Table 1) and can be used to derive analyte cross-reactivities. To enable an assay to be effectively applied in the field, an $IC_{50}$ of less than or about 20 ng/ml, preferably less than or about 10 ng/ml, most preferably less than or about 5 ng/ml, for any individual analyte is preferred. Given the $IC_{50}$ of various analytes, their cross-reactivities, often represented as relative percentages, can be calculated.

The antibody preferably detects Pinaca derivatives of either Structure A, Structure IIIa or Structure IIIb at ≤20 ng/ml, preferably ≤5 ng/ml, more preferably ≤2 ng/ml.

The antibodies of the invention preferably have a cross-reactivity of 100% to AB-Pinaca and greater than 100% cross-reactivity to 1-(5-hydroxypentyl) AB-Pinaca (Structure (6) of FIG. 1), and to 5-fluoropentyl AB-Pinaca (Structure (2) of FIG. 1) and less than 100% to AB-Pinaca pentanoic acid (Structure (5) of FIG. 1) and AB-Fubinaca (Structure (3) of FIG. 1).

The antibodies of the invention preferably have a cross-reactivity of 100% to AB-Pinaca and greater than 100% cross-reactivity to 1-(5-hydroxypentyl) AB-Pinaca (Structure (6) of FIG. 1), and to 5-fluoropentyl AB-Pinaca (Structure (2) of FIG. 1) and less than 75% to AB-Fubinaca (Structure (3) of FIG. 1).

In another embodiment, the antibodies of the invention have 100% cross reactivity to AB-Pinaca N-Pentanoic acid, and greater than 50% cross-reactivity to AB-Pinaca, 4-Hydroxypentyl AB-Pinaca, 5-Hydroxypentyl AB-Pinaca, and 5-Fluoropentyl AB-Pinaca.

In another embodiment, the antibodies of the invention have 100% cross reactivity to AB-Pinaca N-Pentanoic acid, and greater than 75% cross-reactivity to 4-Hydroxypentyl AB-Pinaca, 5-Hydroxypentyl AB-Pinaca, and 5-Fluoropentyl AB-Pinaca.

In another embodiment, the antibodies of the invention have 100% cross reactivity to AB-Pinaca N-Pentanoic acid, and greater than 50% cross-reactivity to AB-Pinaca, 4-Hydroxypentyl AB-Pinaca, 5-Hydroxypentyl AB-Pinaca, and 5-Fluoropentyl AB-Pinaca and less than 50% cross reactivity to AB-Fubinaca.

In another embodiment, the antibodies of the invention have 100% cross reactivity to AB-Pinaca N-Pentanoic acid, and greater than 75% cross-reactivity to 4-Hydroxypentyl AB-Pinaca, 5-Hydroxypentyl AB-Pinaca, and 5-Fluoropentyl AB-Pinaca and less than 50% cross reactivity to AB-Fubinaca.

In another embodiment, the antibodies of the invention have 100% cross reactivity to AB-Pinaca N-Pentanoic acid, and 90% to 110% cross-reactivity to 5-Fluoropentyl AB-Pinaca.

In another embodiment, the antibodies of the invention have 100% cross reactivity to AB-Pinaca N-Pentanoic acid, and 90 to 110% cross-reactivity to 5-Fluoropentyl AB-Pinaca and less than 50% cross reactivity to AB-Fubinaca.

Alternatively or additionally, the antibodies of the invention have less than 1% cross-reactivity with JWH-018 at a concentration of 100 ng/ml.

The terms "5-fluoropentyl AB-Pinaca", "5-F AB-Pinaca" and "5-fluoro AB-Pinaca" can be used interchangeably.

The terms "1-(5-Hydroxypentyl) ABPinaca" and "5 Hxdroxypentyl AB Pinaca" can be used interchangeably.

The terms "1-(4-Hydroxypentyl) ABPinaca" and "4Hxdroxypentyl AB Pinaca" can be used interchangeably.

In yet another embodiment, the antibodies of the invention have an $IC_{50}$ of less than about 20 ng/ml to AB Pinaca, 1-(5-Hydroxypentyl) AB-Pinana, 5-Fluoro AB-Pinaca, AB-Pinaca N-Pentanoic acid and AB-Fubinaca.

In yet another embodiment, the antibodies of the invention have an $IC_{50}$ of less than about 10 ng/ml to AB Pinaca, 1-(5-Hydroxypentyl) AB-Pinana, 5-Fluoro AB-Pinaca, AB-Pinaca N-Pentanoic acid and AB-Fubinaca.

In yet another embodiment, the antibodies of the invention have an $IC_{50}$ of less than about 5 ng/ml to AB Pinaca, 1-(5-Hydroxypentyl) AB-Pinana, 5-Fluoro AB-Pinaca, AB-Pinaca N-Pentanoic acid and AB-Fubinaca.

In yet another embodiment, the antibodies of the invention have an $IC_{50}$ of less than about 2 ng/ml to AB Pinaca, 1-(5-Hydroxypentyl) AB-Pinana, 5-Fluoro AB-Pinaca, AB-Pinaca N-Pentanoic acid and AB-Fubinaca.

Due to inter-molecular attractive forces such as hydrogen bonding and van der Waal's forces there is often a degree of binding or affinity between two molecules whatever their respective structures; the skilled person recognizes that no cross-reactivity or minimal cross-reactivity implies that in the context of a working immunoassay any binding or interaction between an antibody and non-target analytes is at such a low level that it does not compromise the integrity of the immunoassay i.e. false positives are avoided.

Molecules present in solutions or in vitro biological samples which show cross-reactivity towards the antibody can be detected by immunoassays incorporating said antibodies.

The term "able to bind to" or "capable of binding" as used herein means that under standard immunoassay conditions, for example as described in 'Immunoassay: A practical guide' by Brian Law, Taylor and Francis Ltd (ISBN 0-203-48349-9), the antibodies will bind to said molecules. Due to inter-molecular attractive forces such as hydrogen bonding and van der Waal's forces, there is often a degree of binding or affinity between two molecules whatever their respective structures; the skilled person recognizes that no cross-reactivity or minimal cross-reactivity implies that that, in the context of a working immunoassay, any binding or interaction between an antibody and non-target analytes is at such a low level that it does not compromise the integrity of the immunoassay i.e., false positives are avoided.

A further aspect of the current invention is an antibody raisable from an immunogen described above.

The term "antibody" as used herein refers to an immunoglobulin or immunoglobulin-like molecule. In a one embodiment, the antibodies are polyclonal antibodies. However, the skilled person will understand that any type of immunoglobulin molecule or fragment thereof can be used, for example monoclonal antibodies, Fab fragments, scFv fragments and any other antigen binding fragments all of which fall within the scope of the current invention. The polyclonal antibodies may be produced by any method as known to those skilled in the art. Any suitable host animal may be used in the immunisation process including a mammalian animal for example, but not limited to, sheep, rabbit, mouse, guinea pig or horse. In addition, the antibodies may be in the form of polyclonal antisera.

The term "raisable" means that the antibody can be raised from an immunogen of the second aspect of the current invention but is not necessarily so raised. In this context, "raisable" includes, but is not limited to, "raised".

When used in reference to an antibody, the word "specific", "specifically" or "specificity" in the context of the current invention refers to the analyte or analytes that are bound by the antibody, as gauged by a suitable metric such as the sensitivity and cross-reactivity.

For purposes of comparison, one analyte with high cross-reactivity is generally given a value of 100%, with all other analytes accorded a value relative to this; in addition, as is known by one skilled in the art, for cross-reactivity to be of practical use the analyte specific antibody must display a high sensitivity as measured by a suitable metric such as the $IC_{50}$. The $IC_{50}$ is a commonly used indicator of antibody sensitivity for immunoassays. To enable an assay to be effectively applied in the field, an $IC_{50}$ of less than or about 20 ng/ml, less than or about 10 ng/ml, less than or about 5 ng/ml, and or less than about 2 ng/ml for any individual analyte. Given the $IC_{50}$ of various analytes, their cross-reactivities, often represented as relative percentages, can be calculated.

The antibodies of the invention can be adsorbed on, or attached (covalently) to, a substrate. The substrate can be any substance or shape to which an antibody or antibody derivative can bind, either through chemical bonds (before which the substrate has to be chemically activated) or passive adsorption through mutual attraction of the substrate and antibody. In one embodiment, the antibodies are chemically bonded to the chemically activated substrate. The substrate can be for example plastic or magnetic beads, polystyrene microtitre plates (ELISA plates), planar nitrocellulose, a ceramic biochip or a biochip such as a plastic, glass or ceramic biochip surface-coated with a material that facilitates the immobilisation of the antibodies to the substrate. The antibodies or the substrate comprising the antibodies can be provided as discrete off-the-shelf reagents or be incorporated in a kit which optionally has other components such as a conjugate and/or calibrators.

The invention also describes a method of detecting or determining a compound comprising structure IIIa or IIIb in an in vitro sample or in a solution comprising contacting the sample or solution with a detecting agent and an antibody of the invention, detecting the bound detecting agent and deducing the presence of a compound comprising structure IIIa or b. The invention also describes a method of detecting or determining a compound comprising structure IIIa or IIIb in an in vitro sample or in a solution comprising contacting the sample or solution with a detecting agent and an antibody of the invention, wherein both the compound and the detecting agent bind to the antibody; and detecting or determining the amount of detecting agent bound to the antibody. By "detecting" is meant qualitatively analysing for the presence or absence of a substance; by "determining" is meant quantitatively analysing for the amount of a substance present.

The compounds comprising structure IIIa or IIIb which are detected or determined are preferably one or more of AB-Pinaca, AB-Fubinaca, ADB Fubinaca (Structure (4) of FIG. 1), AB-Pinaca pentanoic acid, 1-(5-hydroxypentyl) AB-Pinaca and 5-fluoropentyl AB-Pinaca (synonym 5-F-AB-Pinaca).

In another embodiment, the compounds are one or more of AB-Pinaca, AB-Fubinaca, AB-Pinaca pentanoic acid, AB Fubinaca pentanoic acid, 1-(5-hydroxypentyl) AB-Pinaca, 1-(5-hydroxypentyl) AB-Fubinaca, 5-fluoropentyl AB-Pinaca and 5-fluoropentyl AB-Fubinaca.

In yet another embodiment, the compounds are one or more of AB-Pinaca, AB-Pinaca pentanoic acid, 1-(5-hydroxypentyl) AB-Pinaca, 1-(4-hydroxypentyl) AB-Pinaca, and 5-fluoropentyl AB-Pinaca.

In yet another embodiment, the compounds are one or more of AB-Pinaca, 1-(5-hydroxypentyl) AB-Pinaca, 1-(4-hydroxypentyl) AB-Pinaca, and 5-fluoropentyl AB-Pinaca.

In one embodiment, the detecting agent is:

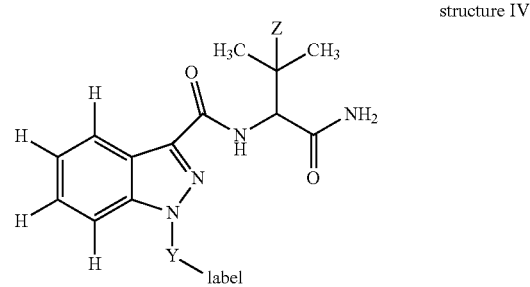

structure IV wherein: Z is H or CH$_3$; Y is a crosslinking group; and label is an labelling agent. In another embodiment, Y is -(A)$_n$-B-D-; A is a functional group or heteroatom enabling attachment of the crosslinking group to the indazole; B is a C$_{1-10}$ substituted or unsubstituted alkylene moiety optionally incorporating an aryl, cycloalkyl and/or a heterocyclic moiety; D is a functional group or heteroatom enabling attachment of the crosslinking group to the labelling agent; and n=0 or 1. In yet another embodiment, n=0; and D is —C(O)—, —NH—, —C═, —C(O)—NH—, —C(O)—NH—CH(COOH)—CH$_2$—CH$_2$—S—, —C(O)—NH—CH(COOH)—CH$_2$—CH$_2$—S-maleimide- or —S—.

The detection or determination step is usually effected with the aid of a calibrator. A calibrator is well known in the art and refers to a reference value or values, the reference being a substance which enables a threshold concentration or the exact or calibrator equivalent amount of analyte(s) to be determined. The determination of an exact or calibrator equivalent amount of analyte(s) usually requires the construction of a calibration curve (also known as a standard curve). The number of calibrator points can vary, but is usually from 5 to 9. To enable a practical assay for clinical/commercial use, the binding of the antibody to the analyte(s) must be such that the concentration at which the analytes are detected or determined is at an acceptable level. The detecting agent (also known as a tracer or conjugate) is the substance which emits a detectable signal and comprises a moiety of similar structure to a target analyte conjugated, by way of a crosslinker, to a labelling agent, that is able to bind to one of the antibodies of the invention; its structure preferably comprises a tracer derived from either Example 7 or 8 of the General Methods, Results and Examples section. The labelling agent, a component which is standard in the art, is selected from an enzyme, a luminescent substance, a radioactive substance, or a mixture thereof. Preferably, the labelling agent is an enzyme, preferably a peroxidase, most preferably horseradish peroxidase (HRP). Alternatively, or additionally, the luminescent substance may be a bioluminescent, chemiluminescent or fluorescent material.

In another embodiment, the presence of detecting agent linked to the antibody can be detected or determined in between about 2 hours and about 10 minutes, between about 1 and a half hours and about ten minutes, or between about 1 hour and 20 minutes. In yet another the presence of detecting agent linked to the antibody can be detected or determined within about 30 minutes.

The invention further describes a kit comprising an antibody of the invention. Preferably, the antibodies engage with a substrate by, for example, passive adsorption or can be chemically bonded to the substrate attached by way of, for example, covalent bonds. Such covalent bonding generally requires the initial introduction of a chemically active compound covalently attached to the substrate surface prior to antibody addition. The antibody itself may also require the addition of a chemical activating group to achieve substrate bonding. These requirements are well known in the art. The substrate can be any medium capable of adsorbing or bonding to an antibody, for example a bead or nanoparticle (optionally chemically-activated), but is preferably of a planar conformation (optionally chemically-activated) such as a biochip. A biochip is a thin, wafer-like substrate with a planar surface which can be made of any suitable material such as glass or plastic but is preferably made of ceramic. The biochip is able to be chemically-activated prior to antibody bonding or is amenable to the passive adsorption of antibodies. The skilled person in biochip development for immunoassay application will recognize that a planar surface at high resolution e.g. if using a scanning electron microscope, is not perfectly 'flat' but will possess an uneven surface, the important aspect being that the 'approximately' planar surface is suitable for application. A microlayer coating of material can optionally be added to the planar surface of the substrate prior to antibody placement. Either the upper surface or both surfaces of the substrate can be coated. The chip can be integrated into or placed into a device with walls. Such a walled device can aid in the retention of added sample or solution.

Therefore, another aspect of the invention is a solid state device, preferably a biochip which is preferably ceramic, which supports an antibody of the invention. The solid state device can also support other antibodies which have a binding specificity which is different from the binding specificity of the antibodies of the invention. Such a support with multiple different antibodies is often described as a multianalyte array (Reference to an 'array' includes a microarray). If the method of detection is different fluorescent labels, each different fluorescent label emitting electromagnetic radiation at a unique wavelength, then the location of placement of the antibodies on the solid substrate is not critical. However, for antibodies forming part of a multianalyte array in which the detectable label is, for example, a chemiluminescent molecule, the antibodies of differing specificity must not overlap and must be located in discrete areas on the solid state device. Such a system is also referred to as a spatially addressable multianalyte array.

For the purposes of the invention, the sample to be used for in vitro analysis can be any sample from which a SC compound can be detected, for example hair or a biological sample. The term "biological sample", as used herein, includes, without limitation, cell cultures or extracts thereof; biopsied material obtained from a mammal or extracts thereof; blood, saliva, urine, faeces, semen, tears, or other body fluids or extracts thereof. In one embodiment, the biological sample is a peripheral biological fluid, but is including whole blood, serum, plasma, hair or urine. The sample may also be a solution which is suspected of containing a drug.

The "detecting agent" is a small molecule (generally of similar structure to a molecule to be detected), which is conjugated to a labelling agent that is able to bind to one of the antibodies of the invention. Alternative names for the "detecting agent" are the "conjugate" or "tracer". The labelling agent is selected from an enzyme, a luminescent substance, a radioactive substance, or a mixture thereof. In one embodiment, the labelling agent is an enzyme, for example a peroxidase, most specifically horseradish peroxidase (HRP). Alternatively, or additionally, the labelling agent is a luminescent substance which may be a bioluminescent, chemiluminescent or a fluorescent material. In one embodiment, for the immunoassay method of the invention, the detecting agent is based on a compound with a substituted-cathinone substructure conjugated to an enzyme or fluorescent molecule. The detection method can be an ELISA but any suitable immunoassay method may be used, for example, a radioimmunoassay, magnetic immunoassay or a lateral flow test. The antibody can be attached to a solid support, for example, a biochip.

The term "subject" refers to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In another embodiment, the subject is a "human".

Enzyme Immunoassays, ELISAs

The enzyme-linked immunosorbent assay (ELISA) is a test that uses antibodies and colour change to identify a substance.

Antigens from the sample are attached to a surface. Then, a further specific antibody is applied over the surface so it can bind to the antigen. This antibody is linked to an enzyme, and, in the final step, a substance containing the enzyme's substrate is added. The subsequent reaction produces a detectable signal, most commonly a colour change in the substrate.

Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed to remove any proteins or antibodies that are not specifically bound. After the final wash step, the plate is developed by adding an enzymatic substrate to produce a visible signal, which indicates the quantity of antigen in the sample.

Lateral Flow Devices

In recent years, the in vitro diagnostics industry has made enormous efforts to develop immunochromatographic tests. Such tests have found applications in both clinical and non-clinical fields. A clinical utility of this test format is particularly suited to point of care utilities.

Rapid immunochromatographic test devices, e.g. in the form of a test strip, are made up of a number of components. Such a test strip commonly includes a sample pad, a conjugate pad, a membrane, e.g. a nitrocellulose membrane, and an absorbent pad. The membrane is usually attached by means of an adhesive to a supporting backing, e.g. made of plastic. In practice, the user dispenses a patient sample (such as urine or whole blood) onto the sample pad. The sample then flows through the sample pad into the conjugate pad, where it mixes with, and releases, the detector reagent. This mixture then flows across the membrane, where it binds with the test and control reagents located in the capture test zone (sample zone) and negative control zone, respectively. When the mixture binds to the reagent that forms the test line, a positive result is indicated. The colour intensity of the test line is proportional to the concentration of analyte in the sample. Excess sample that flows beyond the test and control zones is taken up in the absorbent pad.

Rapid immunochromatographic test devices for diagnostic purposes are easy to operate and thus do not only contribute to the comfort of professional users, e.g. medical stuff, but also allow the operation by non-professionals users, e.g. most patients.

Biochips

Biochips are components used for example in chemical analysis (including Proteomic and Molecular analysis) either to host a test reaction and/or to supply samples under test or reagents. Generally, a Biochip comprises a solid substrate, on which is arranged one or more test sites at which a reaction can take place in use. For instance, the test site may carry one or more reagents (e.g. ligands such as antibodies or antigens) adsorbed to the substrate, which are activated by the addition of a sample substance (e.g. analytes present in the sample bind to specific ligands). Such chips are sometimes referred to as a "lab on a chip" and can also incorporate tools for controlling steps of a reaction. As an example, one Biochip supplied by Randox Laboratories Limited (55 Diamond Road, Crumlin, County Antrim, United Kingdom, BT29 4QY) is used as a medium for performing multiplex analysis of biological samples using a chemiluminescence method. In this example, the Biochip takes the form of a small ceramic chip with a specialised surface preparation which is sensitive to environmental degradation. Therefore the Biochip is generally delivered in an environmentally sealed format, usually evacuated, sealed foil bags.

For instance, the Evidence™ analyser by Randox Laboratories Ltd uses biochips which are fitted into a plastic holder defining three recesses arranged in a line. Each recess is approximately square and sized to just accommodate a biochip, which is also square, with a small clearance to allow the chip to be placed. The "strip" of three mounted biochips is placed within a sealed foil bag for storage, which is then opened when the biochips are required for use. The plastic holder may be placed on a carrier alongside two further strips of three biochips to form a 3×3 array of biochips. The carrier has a keying feature for engagement with a robotic arm such that the array can be transported within the analyser via robotic handling. This configuration is useful for batch analysis.

A "Biochip" is a general term for a reaction platform for hosting chemical, biochemical, proteomic or molecular tests, as may be required for medical diagnosis, drug detection, etc. Typically, a Biochip comprises an inert substrate, such as silicon or glass (often of the order of about 1 cm² or less in surface area), on which one or a plurality of reaction sites is provided. The sites generally carry one or more ligands, for example, one or more antibodies, selected for the test (or "assay") to be performed, adsorbed to the surface of the chip for activation upon combination with a sample applied to the chip (e.g. a blood sample) and/or a reagent. The reactions can be detected using a number of alternative techniques, including detection of chemiluminescence generated by the reaction. Some biochips carry a very large number (hundreds or thousands) of such tests sites, typically arranged in a grid or array, making it possible to carry out numerous assays simultaneously, and using the same single specimen.

STATEMENTS OF THE INVENTION

1. In one embodiment, the invention is an immunogen of structure I

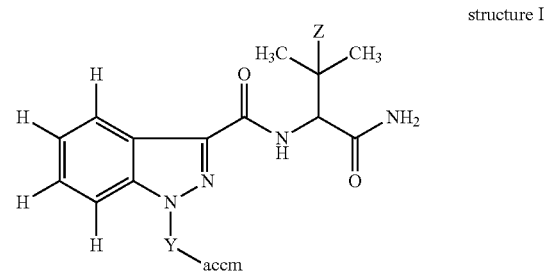

structure I

In which Z is H or $CH_3$; Y is a crosslinking group and accm is an antigenicity-conferring carrier material.

2. In another embodiment, the invention is an immunogen of statement 1 in which Y is -(A)$_n$-B-D- in which B is a C$_{1-10}$, preferably a C$_3$ or a C$_{1-6}$ substituted or unsubstituted alkylene moiety optionally incorporating a cycloalkyl and/or a heterocyclic moiety; n=0 or 1 and A is a functional group or heteroatom enabling attachment of the crosslinker to the N-atom of the heterocycle and D is a functional group or heteroatom enabling attachment of the crosslinker to the antigenicity-conferring carrier material.

3. In another embodiment, the invention is an immunogen of statement 2 in which n=0 and the functional group or heteroatom D is —C(O)—, —NH—, —C═, or —S—; or in which n=1 and the functional group or heteroatom A is —C(O)— or —C(O)—O—; and the functional group or heteroatom D is —C(O)—, —NH—, —C═, or —S—.

4. In another embodiment, the invention is a compound of structure II

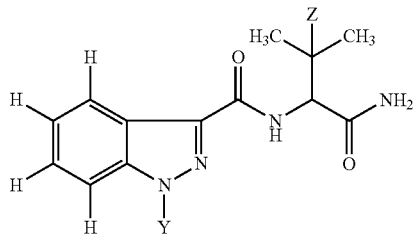

structure II in which Z is H or CH$_3$; Y is -(A)$_n$-B-D in which n=0 or 1, A is attached to the N-atom of the heterocycle and is —C(O)— or —C(O)—O—; B is a C$_{1-10}$, preferably a C$_3$ or C$_{1-6}$ substituted or unsubstituted alkylene moiety optionally incorporating a cycloalkyl and/or a heterocyclic moiety; and D is a functional group.

5. In another embodiment, the invention is a compound of statement 4 in which the functional group D is —CHO, —NH$_2$, —CO$_2$H, —CO$_2$Me, —CO$_2$Et, —CO$_2$Pr, —CO$_2$isoPr, —CO$_2$But, —CO$_2$isoBut, —CO$_2$tertBut or —SH; or in which n=0 and the functional group D is —CHO, —NH$_2$, —CO$_2$H, —CO$_2$Me, —CO$_2$Et, —CO$_2$Pr, —CO$_2$isoPr, —CO$_2$But, —CO$_2$isoBut, —CO$_2$tertBut or —SH.

6. In another embodiment, the invention is a method of synthesising a compound of statement 5 in which D is —CO$_2$Me, —CO$_2$Et, —CO$_2$Pr, —CO$_2$isoPr, —CO$_2$But, —CO$_2$isoBut or —CO$_2$tertBut; or in which n=0, B is a C$_{1-6}$ alkylene moiety and D is —CO$_2$Me, —CO$_2$Et, —CO$_2$Pr, —CO$_2$isoPr, —CO$_2$But, —CO$_2$isoBut or —CO$_2$tertBut comprising
  i) alkylating 3-carboxyindazole by reaction with a terminally halogenated alkylene ester in which the alkyene moiety is C$_{1-6}$ and the ester moiety is —CO$_2$Me, —CO$_2$Et, —CO$_2$Pr, —CO$_2$isoPr, —CO$_2$But, —CO$_2$isoBut or —CO$_2$tertBut, and
  ii) reacting the product of i) with valinimide; or comprising
  i) alkylating 3-carboxyindazole with a terminally halogenated alkylene ester in which the alkyene moiety is C$_{1-6}$ and the ester moiety is —CO$_2$Me, —CO$_2$Et, —CO$_2$Pr, —CO$_2$isoPr, —CO$_2$But, —CO$_2$isoBut or —CO$_2$tertBut, and
  ii) reacting the product of i) with valinimide.

7. In another embodiment, the invention is a method of statement 6 comprising a further step in which the ester group is hydrolysed.

8. In another embodiment, the invention is an antibody which binds or specifically binds to an epitope of structure III

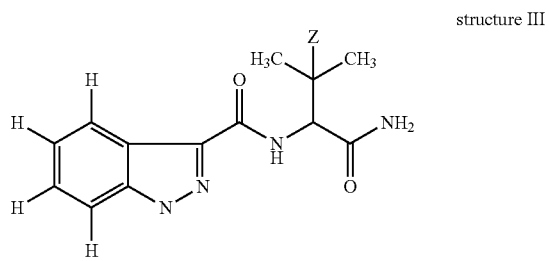

structure III

In which Z is H or CH$_3$.

9. In another embodiment, the invention is an antibody of statement 8 which is derived from an immunogen of any of statements 1 to 3.

10. In another embodiment, the invention is a antibody of statements 8 and 9 which has a cross-reactivity of 100% to AB-Pinaca and greater than 100% cross-reactivity to 1-(5-hydroxypentyl) AB-Pinaca, and 5-fluoropentyl AB-Pinaca and less than 100% to AB-Pinaca pentanoic acid and AB-Fubinaca.

11. In another embodiment, the invention is a method of detecting or determining a compound comprising structure III in an in vitro sample or in a solution comprising contacting the sample or solution with a detecting agent and an antibody of statements 8 or 9, detecting the bound conjugate and deducing the presence of a compound comprising structure III.

12. In another embodiment, the invention is a method of statement 11 in which the compounds are one or more of AB-Pinaca, AB-Fubinaca, AB-Pinaca pentanoic acid, AB Fubinaca pentanoic acid, 1-(5-hydroxypentyl) AB-Pinaca, 1-(5-hydroxypentyl) AB-Fubinaca, 5-fluoropentyl AB-Pinaca and 5-fluoropentyl AB-Fubinaca; or the compounds are one or more of AB-Pinaca, AB-Fubinaca, ADB-Fubinaca, AB-Pinaca pentanoic acid, 1-(5-hydroxypentyl) AB-Pinaca and 5-fluoropentyl AB-Pinaca.

13. In another embodiment, the invention is a kit comprising an antibody of any of statements 8 to 10.

14. In another embodiment, the invention is a kit of statement 13 in which the antibody is adsorbed on or attached.

General Methods, Examples and Results
Preparation of Haptens, Immunogens and Detecting Agents In immunology, haptens are defined as substances which by themselves cannot elicit immune responses; they require chemical coupling to larger immunogenic molecules (antigenicity conferring carrier materials or 'accm'), to be capable of inducing an immune response. Appropriate accms commonly contain poly(amino acid) segments and include polypeptides, proteins and protein fragments. Illustrative examples of antigenicity conferring carrier materials are keyhole limpet haemocyanin (KLH), bovine thyroglobulin (BTG), bovine serum albumin (BSA), egg ovalbumin, bovine gamma globulin or cationised BSA. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof. Conjugation of haptens can be performed using standard methods of conjugation such as mixed anhydride, EDC or succinimidyl activation of the haptens. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS).

General Procedure for MALDI-TOF Analysis of Immunogens

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of sinapinic acid and bovine serum albumin (Fluka) was used as an external calibrant.

Preparation of Antisera

In order to generate polyclonal antisera, an immunogen of the present invention is mixed with Freund's adjuvant and the mixture is injected into a host animal, such as rabbit, sheep, mouse, guinea pig or horse. Sheep are the preferred host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding. In one embodiment, the purification is by immunoglobulin precipitation, antigen-specific affinity purification, column chromatography, such as, size-exclusion chromatography or ion exchange chromatography.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunising an animal, preferably a mammalian animal, by repeated administration of an immunogen. The serum from the immunised animal is collected when the antibody titre is sufficiently high. A detecting agent is added to a sample containing the target analyte and the raised antibodies, and the detecting agent and analyte compete for binding to the antibodies. The process may comprise fixing said serum antibodies to a solid state device such as a polystyrene support or a ceramic chip. The antibodies can be polyclonal or monoclonal using standard techniques, but the current invention makes use of polyclonal antibodies. The signal emitted in the immunoassay is proportionate to the quantity of detecting agent bound to the antibodies which in turn is inversely proportionate to the analyte concentration. The signal can be detected or quantified by comparison with a calibrator.

Example 1: Synthesis of 1-(5-ethoxy-5-oxopentyl)-1H-indazole-3-carboxylic acid 2 (FIG. 2)

Indazole-3-carboxylic acid 1 (3.09 g, 19.1 mmol) was dissolved in DMF (80 ml) and the solution cooled to 0° C. Sodium hydride (3.9 g, 58.5 mmol) was then added portionwise and the mixture was heated to 60° C. for 30 minutes and then cooled to room temperature. Ethyl-5-bromovalerate (5 ml, 31.2 mmol) in DMF (10 mL) was added drop-wise and the mixture was stirred at 60° C. overnight. The mixture was cooled to room temperature and concentrated in vacuo. To the crude reside obtained was added water and ethyl acetate. The aqueous mixture was then acidified to pH 4 and extracted with ethyl acetate added (2×100 ml). The combined organic layers were dried over sodium sulphate, filtered and concentrated in vacuo. The crude residue was purified by column chromatography using chloroform as eluent to give 1-(5-ethoxy-5-oxopentyl)-1H-indazole-3-carboxylic acid 2 as a clear oil (2.43 g, 44%).

Example 2: Synthesis of ethyl 5-[3-(1-amino-3-methyl-1-oxobutan-2-yl)carbamoyl)-1H-indazol-1-yl]pentanoate 3 (FIG. 2)

EDC.HCl (2.4 g, 12.5 mmol), L-valinimide HCl (1.94 g, 12.7 mmol), HOBt hydrate (1.96 g, 12.6 mmol) and DIPEA (7.2 ml, 42 mmol) were added to a solution of 1-(5-ethoxy-5-oxopentyl)-1H-indazole-3-carboxylic acid 2 (2.43 g, 8.4 mmol) in DMF (40 ml) and the mixture was stirred at room temperature overnight under nitrogen. The solvent was removed in vacuo and the crude residue dissolved in water (100 ml) and extracted with ethyl acetate (3×50 ml). The combined organic layers were washed by brine (10 0 ml), dried over sodium sulphate, filtered and concentrated in vacuo. The crude product obtained was purified by column chromatography using 10% MeOH/chloroform to give ethyl 5-[3-((1-amino-3-methyl-1-oxobutan-2-yl)carbamoyl)-1H-indazol-1-yl]pentanoate 3 (2.43 g, 75%) as yellow oil.

Example 3: Synthesis of AB-Pinaca Pentanoic Acid 4 (Hapten-1) (FIG. 2)

A solution of potassium hydroxide (0.86 g) in water (2 5 ml) was added to a solution of ethyl 5-[3-((1-amino-3-methyl-1-oxobutan-2-yl) carbamoyl)-1H-indazol-1-yl]pentanoate 3 (2.43 g, 6.26 mmol) in THF (25 ml) and the solution was stirred at room temperature for 2 hours. The solvents were removed in vacuo and the remaining aqueous mixture was acidifed to pH 4-5. The aqueous layer was extracted with ethyl acetate (3×100 ml) and the combined organics layers were washed by brine (100 ml), dried over sodium sulphate and concentrated in vacuo to give crude product as a semisolid. The product was recrystallised from ethyl acetate/hexane and the white solid was filtered off and washed with diethyl ether to give AB-Pinaca pentanoic acid 4 (Hapten-1) (1.66 g, 74%). NMR 13C (DMSO d6): 174.26, 172.71, 161.37, 140.63, 136.46, 126.70, 122.54, 121.98, 121.68, 110.46, 56.86, 48.48, 33.09, 31.24, 28.91, 21.75, 19.39, 18.00.

Example 4: Synthesis of AB-Pinaca Pentanoic Acid) HCTL 5 (Hapten-2) (FIG. 3)

To a solution of AB-Pinaca pentanoic acid 4 (496.3.4 mg, 1.38 mmol) in pyridine (40 ml) was added EDC.HCl (437 mg, 2.28 mmol) and HCTL.HCl (homocysteinethiolactone-.HCl) (368 mg, 2.39 mmol) and the mixture was stirred at room temperature overnight. TLC showed complete consumption of starting material and the solvent was removed in vacuo. The crude mixture obtained was dissolved in water (50 ml) and the product was extracted with ethyl acetate (3×50 ml). The combined organic layers were washed by water (50 ml), brine (50 ml), dried over sodium sulphate, filtered and concentrated to dryness. The product was purified by column chromatography using 15% MeOH/ethyl acetate to give AB-Pinaca pentanoic acid HCTL 5 (Hapten-2) as an off-white solid.

Example 5: Conjugation of AB-Pinaca Pentanoic Acid 4 (Hapten-1) to BSA (Immunogen-1)

To a solution of AB-Pinaca pentanoic acid 4 (Hapten-1) (27.7 mg) in DMF (1.0 ml) was added N-(3-Dimethylaminopropyl)-N'-ethylcarbodiimide hydrochloride EDC.HCl (73.7 mg) and N-hydroxysuccinimide (44.3 mg) and the mixture was incubated on the roller at room temperature overnight. This solution was added dropwise to a solution of BSA (100 mg, 1.5 mmol) in phosphate buffer saline (50 mM) (pH 8.0) (10 ml). The resulting solution was incubated on the roller at room temperature overnight. Excess hapten was removed by dialysis against phosphate buffer saline, pH 7.2 (3 changes) for 24 hours at 4° C., and freeze-dried. MALDI results showed 24.1 molecule of AB-Pinaca pentanoic acid had been conjugated to one molecule of BSA.

Example 6: Conjugation of AB-Pinaca Pentanoic Acid 4 (Hapten-1) to KLH (Immunogen-2)

To a solution of AB-Pinaca pentanoic acid 4 (Hapten-1) (27.7 mg) in DMF (1.0 ml) was added N-(3-Dimethylaminopropyl)-N'-ethylcarbodiimide hydrochloride EDC.HCl (73.7 mg) and N-hydroxysuccinimide (44.3 mg) and the mixture was incubated on the roller at room temperature overnight. This solution was added dropwise to a solution of KLH (100 mg) in phosphate buffer saline (50 mM) (pH 8.0) (10 ml). The resulting solution was incubated on the roller at room temperature overnight. Excess hapten was removed by dialysis against phosphate buffer saline, pH 7.2 (3 changes) for 24 hours at 4° C., and freeze-dried.

Example 7: Conjugation of AB-Pinaca Pentanoic Acid 4 (Hapten-1) to HRP (Tracer-1)

EDC hydrochloride (1.5 mg) was dissolved in water (0.5 ml) and immediately added to a solution of AB-Pinaca pentanoic acid 4 (Hapten-1) (3 mg) in DMF (0.2 ml). After mixing, this solution was added dropwise to a solution of HRP (20 mg) in water (1 ml). N-hydroxysuccinimide (1 mg) was added and the reaction mixture was incubated in the dark at room temperature overnight. Excess hapten was removed with double PD-10 columns (Pharmacia) in series, pre-equilibrated with PBS at pH 7.2. The hapten-1-HRP conjugate (Tracer-1) was then dialysed overnight against 10 L of PBS at pH 7.2 at 4° C.

Example 8: Conjugation of AB-Pinaca Pentanoic Acid HCTL 5 (Hapten-2) to HRP (Tracer-2)

4-N-Maleimidomethylcyclohexyl-1-carboxylic acid NHS ester solution (0.84 mg) in DMF (0.05 mL) was added drop-wise to HRP (20 mg) dissolved in 50 mM HEPES solution, pH 8.5 (0.8 mL) while stirring. The resulting solution was stirred at room temperature for 40 minutes. Excess 4-N-Maleimidomethylcyclohexyl-1-carboxylic acid NHS ester was removed by dialysis against Phosphate Buffered Saline, pH 7.2. Keep the solution darkened during the processing. AB-Pinaca pentanoic acid HCTL 5 (Hapten-2) (2 mg) was dissolved in DMF (0.2 mL). 0.2 mL of 1M Potassium hydroxide solution was added to the above hapten solution while stirring during 10 minutes period. 0.5 mL of 0.2 M Phosphate buffer, pH 7.0 was then added to quench reaction; 0.15 mL of 1M HCl solution was added to bring pH to 7.0. The maleimide modified HRP was added to the activated hapten, roll for 2 hours at room temperature and then transfer to 4° C. and roll for 16-20 hours. Excess hapten was removed with PD-10 column (Pharmacia), pre-equilibrated with Phosphate Buffered Saline, pH 7.2, followed by dialysis at 2-8° C. against Phosphate Buffered Saline, pH 7.2. Keep the solution darkened during the processing. The KOH solution opens the ring structure below at the thioamide bond and the free —SH group thus formed attaches to maleimide-HRP, i.e. indazole-$(CH_2)_4$—C(O)—NH—CH(COOH)—$CH_2$—$CH_2$—S-maleimide-HRP.

Example 9: Characterisation of Antibodies to AB-Pinaca-KLH (Immunogen 2 of Example 6)

The wells of an enhanced binding 96 well polystyrene microtitre plate were coated with IgG fraction of antiserum raised to AB-Pinaca-KLH (Immunogen 2 of Example 6), diluted in 10 mM Tris, pH8.5 (125 µl/well). The appropriate antibody coating dilution was determined using standard ELISA checkerboard techniques. The plate was incubated for 2 hours at 37° C., washed 4 times over 10 minutes with Tris buffered saline containing Tween 20 (TBST) and tapped dry. Standard solutions of AB-Pinaca pentanoic acid were prepared in TBST at 0, 0.31, 0.63, 1.25, 2.50, 5.0, 10.0 and 20.0 ng/ml, and 50 µl of each was added to the appropriate wells. 75 µl of Tracer-1 (Example 7) diluted in Tris buffer (pH 7.2) containing EDTA, D-mannitol, sucrose, thimerosal and BSA, was added to each of the wells. The appropriate dilution of tracer was also determined using standard ELISA checkerboard techniques. The plate was incubated at 25° C. for 1 hour. Excess unbound tracer was removed by washing 6 times over a 10-15 minute period with TBST and tapped dry. 125 µl of tetramethylbenzidine (TMB) substrate solution was added to each well of the plate that was then incubated for 20 minutes in the dark at room temperature. The reaction was terminated by addition of 125 µl 0.2 M $H_2SO_4$ to each well. The absorbance was measured at 450 nm using a microtitre plate reader. The data generated in the assay is presented in Table 1. In order to determine the specificity of the competitive ELISAs, standard solutions of a range of structurally similar compounds were prepared in TBST. Using calibration curves generated from these compounds (0-20 ng/ml), the cross-reactivity was determined. The results of this study are presented in Table 1.

TABLE 1

Antibody binding characteristics of Pinaca derivatives. Antibody to AB-Pinaca-KLH (raised against immunogen 2 of Example 6); Tracer-1 of Example 7; calibrator is AB-Pinaca pentanoic acid.

| StandardConc ng/ml | AB-Pinaca pentanoic acid OD; B/Bo | AB-Pinaca OD; B/Bo | 1-(5-OHpentyl) AB-Pinaca* OD; B/Bo | 5-fluoro AB-Pinaca OD; B/Bo | AB-Fubinaca OD; B/Bo |
|---|---|---|---|---|---|
| 0 | 2.194; 100.0 | 2.184; 100.0 | 2.053; 100.0 | 2.243; 100.0 | 2.141; 100.0 |
| 0.31 | 1.698; 77.4 | 1.532; 70.1 | 1.415; 68.9 | 1.351; 60.2 | 1.541; 72.0 |
| 0.63 | 1.529; 69.7 | 1.325; 60.7 | 1.163; 56.6 | 1.070; 47.7 | 1.379; 64.4 |
| 1.25 | 1.223; 55.8 | 1.036; 47.4 | 0.896; 43.6 | 0.819; 36.5 | 1.120; 52.3 |
| 2.50 | 0.926; 42.2 | 0.778; 35.6 | 0.690; 33.6 | 0.629; 28.0 | 0.915; 42.7 |
| 5.00 | 0.673; 30.7 | 0.593; 27.2 | 0.504; 24.5 | 0.462; 20.6 | 0.695; 32.4 |

TABLE 1-continued

Antibody binding characteristics of Pinaca derivatives. Antibody to AB-Pinaca-KLH (raised against immunogen 2 of Example 6); Tracer-1 of Example 7; calibrator is AB-Pinaca pentanoic acid.

| StandardConc ng/ml | AB-Pinaca pentanoic acid OD; B/Bo | AB-Pinaca OD; B/Bo | 1-(5-OHpentyl) AB-Pinaca* OD; B/Bo | 5-fluoro AB-Pinaca OD; B/Bo | AB-Fubinaca OD; B/Bo |
|---|---|---|---|---|---|
| 10.00 | 0.465; 21.2 | 0.404; 18.5 | 0.356; 17.3 | 0.326; 14.5 | 0.491; 22.9 |
| 20.00 | 0.317; 14.5 | 0.267; 12.2 | 0.242; 11.8 | 0.227; 10.1 | 0.337; 15.7 |
| IC$_{50}$ | 1.723 ng/ml | 1.107 ng/ml | 0.887 ng/ml | 0.544 ng/ml | 1.546 ng/ml |
| % CR | 64.25 | 100.00 | 124.80 | 203.49 | 71.60 |

*1-(5-hydroxypentyl) AB-Pinaca.
All cross-reactants for antibody binding studies were sourced from Cayman Chemical, Ann Arbor, Michigan, US (Catalogue numbers 14755, 15050, 14038, 15051, 14039).
OD = absorbance at 450 nm
B = absorbance at 450 nm at x ng/ml standard concentration
B$_0$ = absorbance at 450 nm at 0 ng/ml standard concentration
Percentage B/B0 = (B/B0) × 100
IC$_{50}$ = standard concentration which produces 50% inhibition of maximal signal
% CR = percentage cross-reactivity Table 1 shows that the antibody of the invention has a high affinity for various Pinaca derivatives. Modification of the 1-N-alkyl chain of the indazole or of the N-alkyl amido side chain of the 3-substituent of the indazole i.e. a moiety consisting of either 1-amino-1-carbonyl-3-methylbut-2-yl or 1-amino-1-carbonyl-3,3-dimethylbut-2-yl, surprisingly does not significantly affect the binding of the antibody as indicated by the similar IC$_{50}$ values.

Example 10: AB-PINACA ELISA

General

A microtitre plates was precoated with AB-PINACA antibody (raised against immunogen 2 of Example 6). Pinaca derivative (antigen), if present in the sample competes with the horseradish peroxidase labelled AB-PINACA (enzyme labelled antigen, herein Tracer-2 of Example 8) for a limited number of antibody sites on the microtitre plate. After incubation at room temperature to allow a competition reaction to take place, the microtitre plate was washed to remove excess reagents. The enzyme substrate (tracer-2) was added. After an incubation period to allow maximum colour development, the colour reaction was stopped by the addition of acid. This produces a colour change from blue to yellow, and the absorbances are read at 450 nm. A standard curve was then constructed to determine the Pinaca derivative's concentration in the sample.

Urine Sample Preparation
1. The urine samples were centrifuged at 13000 rpm (9500 RCF) for 60 seconds.
2. The centrifuged urine samples were diluted 1:3 with diluted wash buffer/diluent (i.e. 100 µL sample+200 µL diluted wash buffer/diluent).
3. The sample was mixed gently by pipetting without the formation of foam.

Whole Blood Sample Preparation
1. Whole blood samples were diluted 1:4 with diluted wash buffer/diluent (i.e. 50 µL sample+150 µL diluted wash buffer/diluent).
2. The samples were mixed gently by pipetting without the formation of foam.

Procedure

All reagents were left to reach room temperature (+15 to +25° C.) prior to use. In order to minimise edge effects microtitre plate was sealed with an adhesive plate sealer.

The assay was performed in duplicate. The following layout was used for a test plate where each box represents 2 wells.

| S1 | T1 | T9 | T17 | T25 | T33 |
| S2 | T2 | T10 | T18 | T26 | T34 |
| S3 | T3 | T11 | T19 | T27 | T35 |
| S4 | T4 | T12 | T20 | T28 | T36 |
| S5 | T5 | T13 | T21 | T29 | T37 |
| S6 | T6 | T14 | T22 | T30 | T38 |
| QC | T7 | T15 | T23 | T31 | T39 |
| QC | T8 | T16 | T24 | T32 | T40 |

S = Standard
QC = Quality Control
T = Test Sample a) The following was pipetted into the appropriate wells of the microtitre plate:

|  | Standard | Sample | Q.C. |
|---|---|---|---|
| Standard | 50 µL | — | — |
| Sample | — | 50 µL | — |
| Q.C. | — | — | 50 µL |
| Conjugate | 75 µL | 75 µL | 75 µL | b) The microtitre plate was gently tapped plate from side to side for a few seconds.
c) The microtitre plate was covered with a plate sealer before incubating for 30 minutes at room temperature (+15 to +25° C.) in the dark.
d) The plate was inverted and the liquid was tapped out.
e) The plate was washed 6 times with diluted wash buffer (ensuring all wells were filled), over a 10-15 minute period. After the final wash the liquid was discarded and the plate was tapped onto lint free tissue paper until completely dry.
f) Immediately after washing, 125 µL of the one shot substrate II solution was pipetted into each well using a multichannel pipette. The microtitre plate was gently tapped from side to side and incubated for (20±2 minutes) at room temperature (+15 to +25° C.) in the dark.
g) The colour reaction was stopped by the addition of 100 µL of stop solution per well. A colour change from blue to yellow should be evident.

h) The optical density was measured at 450 nm within 10 minutes of stopping the colour reaction. The use of a 630 nm filter is recommended as the reference wavelength, if available.

Standard Curve and Interpretation of Results a) The mean absorbance of the standards, controls and samples were calculated.
b) The absorbances of standards against $\log_{10}$ (standard concentration) were plotted.
c) The control and sample concentrations were read from the standard curve.
d) To obtain concentrations for urine samples in ng/mL, the results were multiplied by 3 to take into account the dilution factor.
e) To obtain concentrations for whole blood samples in ng/mL, the results were multiplied by 4 to take into account the dilution factor.
f) It is recommended that a 4 parameter curve fit method is used when generating the standard curve.

Limits of Detection

| Sample | Limit of Detection |
| --- | --- |
| Urine (1 in 3 dilution) | 0.26 ng/ml |
| Whole blood (1 in 4 dilution) | 0.41 ng/ml |

N = 20 (dilution factor has been applied)

Assay Range/Cut-Off

By applying the provided sample dilution for each matrix, an ELISA kit has been developed to achieve the assay range and cut-off values indicated below. An alternative cut off/sample dilution may be used.

| Sample | Cut Off |
| --- | --- |
| Urine (1 in 3 dilution) | 5.0 ng/ml |
| Whole blood (1 in 4 dilution) | 5.0 ng/ml |

| Standard conc ng/ml | Standard Conc. for urine sample with 1:3 dilution (ng/ml) | Standard Conc. for Blood sample with 1:4 dilution (ng/ml) |
| --- | --- | --- |
| 0.00 | 0.00 | 0.00 |
| 0.06 | 0.19 | 0.25 |
| 0.19 | 0.56 | 0.74 |
| 0.56 | 1.67 | 2.22 |
| 1.67 | 5.00 | 6.67 |
| 5.00 | 15.00 | 20.00 |

Specificity

The specificity of this ELISA kit is summarised in the table below:

| Cross-Reactivity of AB-PINACA related compounds | |
| --- | --- |
| Compound | % Cross-Reactivity |
| AB-PINACA N-Pentanoic acid | 100 |
| 5-Fluoro AB-PINACA | 98.9 |
| 5-Hydroxypentyl AB-PINACA | 83.8 |
| 4-Hydroxypentyl AB-PINACA | 85.2 |
| AB-PINACA | 52.4 |
| AB-FUBINACA | 35.3 |
| ADB-PINACA pentanoic acid metabolite | 32.8 |
| 5-Fluoro AB-PINACA N-(4-hydroxypentyl) metabolite | 24.1 |
| ADB-PINACA N-(5-hydroxypentyl) metabolite | 15.2 |
| 5-Fluoro ADB-PINACA | 9.8 |
| 5-Fluoro ADBICA | 4.7 |
| AB-FUBINACA carboxylic acid | 4.5 |
| AB-CHMINACA | 3.8 |
| ADBICA | 0.7 |
| AB-PINACA carboxylic acid | <1 |
| AKB48 N-(4-hydroxypentyl) metabolite | <1 |
| AKB48 N-(5-hydroxypentyl) metabolite | <1 |
| PB-22 N-(5-hydroxypentyl) metabolite | <1 |
| MN-25 | <1 |
| PB-22 N-Pentanoic acid | <1 |
| AKB48 N-Pentanoic acid metabolite | <1 |
| MN-18 | <1 |
| RCS-4 | <1 |
| 3-OH AKB-48 | <1 |
| SDB-001 N-Pentanoic acid | <1 |
| 3-OH SDB-001 | <1 |
| AB-001 N-Pentanol | <1 |

| Concentration of compounds that elicit a negative response at the indicated concentration | |
| --- | --- |
| Compound | Concentration |
| JWH-007 | 100 ng/ml |
| JWH-015 | 100 ng/ml |
| JWH-018 | 100 ng/ml |
| JWH-019 | 100 ng/ml |
| JWH-073 | 100 ng/ml |
| JWH-081 | 100 ng/ml |
| JWH-200 | 100 ng/ml |
| JWH-203 | 100 ng/ml |
| JWH-210 | 100 ng/ml |
| JWH-398 | 100 ng/ml |
| JWH-018 4-Hydroxyindole | 100 ng/ml |
| JWH-018 5-Hydroxyindole | 100 ng/ml |
| JWH-018 6-Hydroxyindole | 100 ng/ml |
| JWH-018 N-Pentanoic acid | 100 ng/ml |
| JWH-073 4-Hydroxyindole | 100 ng/ml |
| JWH-073 5-Hydroxyindole | 100 ng/ml |
| JWH-073 N-Butanoic acid | 100 ng/ml |
| JWH-073 N-Butanol | 100 ng/ml |
| AM-2201 6-Hydroxyindole | 100 ng/ml |
| JWH-018 N-(5-Hydroxypentyl) | 100 ng/ml |
| JWH-250 N-(5-Carboxypentyl) | 100 ng/ml |
| JWH-250 N-(5-Hydroxypentyl) | 100 ng/ml |
| JWH 250 N-(4-hydroxypentyl) metabolite | 100 ng/ml |
| A-834735 | 100 ng/ml |
| AM-694 | 100 ng/ml |
| AM-2201 | 100 ng/ml |
| AM-2232 | 100 ng/ml |
| RCS-8 | 100 ng/ml |
| STS-135 | 100 ng/ml |
| PB-22 | 100 ng/ml |
| PB-22 3-Carboxyindole metabolite | 100 ng/ml |
| 5-fluoro PB-22 3-carboxyindole | 100 ng/ml |
| BB-22 | 100 ng/ml |
| 5-fluoro PB-22 | 100 ng/ml |
| BB-22 3-Carboxyindole metabolite | 100 ng/ml |
| AB001 N-Pentanoic Acid | 100 ng/ml |
| UR-144 | 100 ng/ml |
| UR-144 N-Pentanoic acid | 100 ng/ml |
| XLR-11 | 100 ng/ml |
| NNEI | 100 ng/ml |

-continued

Concentration of compounds that elicit a negative response at the indicated concentration

| Compound | Concentration |
| --- | --- |
| THJ 2201 | 100 ng/ml |
| Ranitidine HCl | 10 µg/ml |
| Propranolol HCL | 10 µg/ml |
| Metformin HCl | 10 µg/ml |

Precision and % Bias

Typical intra-assay precision is summarised in the table below:

| Standard (ng/mL) | % B/Bo | Number of replicates | % CV |
| --- | --- | --- | --- |
| 0.00 | 100 | 12 | 5.4 |
| 0.06 | 77 | 12 | 3.5 |
| 0.19 | 62 | 12 | 4.1 |
| 0.56 | 50 | 12 | 6.3 |
| 1.67 | 33 | 12 | 5.2 |
| 5.00 | 20 | 12 | 7.1 |

Inter assay precision and % Bias is summarised in the table below. Calculated from 3 replicates over 5 runs for 3 samples (50% below cut off, cut off and 50% above cut off)

| Concentration (ng/mL) | Mean reported Concentration ng/ml | % Bias | % CV |
| --- | --- | --- | --- |
| Urine | | | |
| 2.5 | 2.72 | 8.8 | 7.7 |
| 5 | 5.85 | 17.0 | 6.1 |
| 7.5 | 8.22 | 2.8 | 7.5 |
| Whole Blood | | | |
| 2.5 | 2.19 | −12.4 | 7.0 |
| 5 | 4.56 | −8.8 | 6.9 |
| 7.5 | 8.81 | 17.5 | 7.0 |

The cross-reactivity data between Examples 9 and 10 vary due to variations in experimental technique including the choice or tracer (or detecting agent). The data presented in Example 10 is from a final validated assay.

The invention claimed is:

1. A polyclonal antibody, wherein the polyclonal antibody is raised against an immunogen having the structure of:

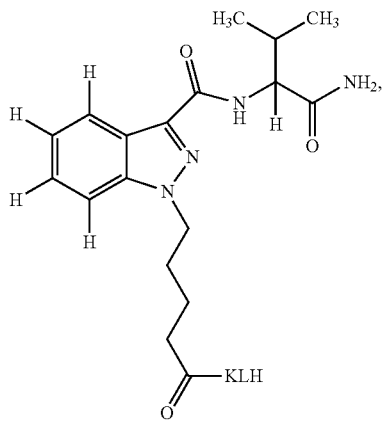

wherein KLH is keyhole limpet hemocyanin,
wherein the polyclonal antibody has an $IC_{50}$ value of:
   1.723 ng/ml to AB-Pinaca N-pentanoic acid;
   0.544 ng/ml to 5-fluoropentyl AB-Pinaca;
   0.887 ng/ml to 1-(5-hydroxypentyl) AB-Pinaca;
   1.107 ng/ml to AB-Pinaca; and
   1.546 ng/ml to AB-Fubinaca;
wherein the $IC_{50}$ values are determined using a tracer having the structure of:

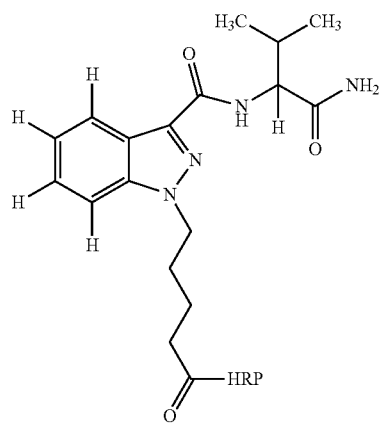

wherein HRP is horseradish peroxidase and HRP is a detectable label.

2. A kit comprising the polyclonal antibody of claim 1.

3. A polyclonal antibody, wherein the polyclonal antibody is raised against an immunogen having the structure of:

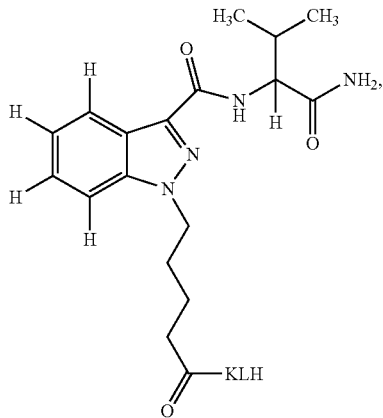

wherein KLH is keyhole limpet hemocyanin,
wherein the polyclonal antibody exhibits the following percent cross-reactivities for the compounds listed in the table below, when compared with 100% cross reactivity for AB PINACA N-pentanoic acid:

| Compound | % Cross-Reactivity |
| --- | --- |
| 5-Fluoro AB-PINACA | 98.9 |
| 5-Hydroxypentyl AB-PINACA | 83.8 |
| 4-Hydroxypentyl AB-PINACA | 85.2 |
| AB-PINACA | 52.4 |
| AB-FUBINACA | 35.3 |

-continued

| Compound | % Cross-Reactivity |
|---|---|
| ADB-PINACA pentanoic acid metabolite | 32.8 |
| 5-Fluoro AB-PINACA N-(4-hydroxypentyl) metabolite | 24.1 |
| ADB-PINACA N-(5-hydroxypentyl) metabolite | 15.2 |
| 5-Fluoro ADB-PINACA | 9.8 |
| 5-Fluoro ADBICA | 4.7 |
| AB-FUBINACA carboxylic acid | 4.5 |
| AB-CHMINACA | 3.8 |
| ADBICA | 0.7 |
| AB-PINACA carboxylic acid | <1 |
| AKB48 N-(4-hydroxypentyl) metabolite | <1 |
| AKB48 N-5-hydroxypentyl) metabolite | <1 |
| PB-22 N-(5-hydroxypentyl) metabolite | <1 |
| MN-25 | <1 |
| PB-22 N-Pentanoic acid | <1 |
| AKB48 N-Pentanoic acid metabolite | <1 |
| MN-18 | <1 |
| RCS-4 | <1 |
| 3-OH AKB-48 | <1 |
| SDB-001 N-Pentanoic acid | <1 |
| 3-OH SDB-001 | <1 |
| AB-001 N-Pentanol | <1 | wherein the cross-reactivities are determined by using a tracer having the structure of:

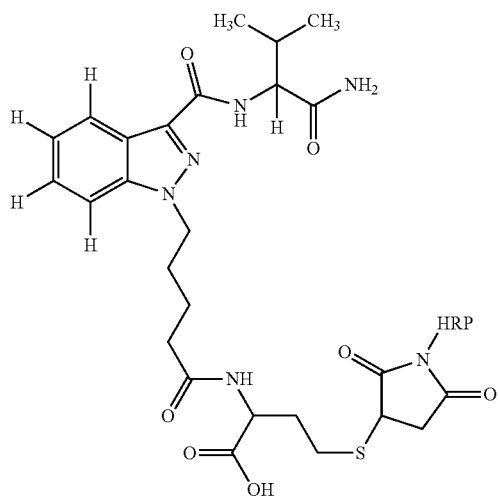

wherein HRP is horseradish peroxidase and HRP is a detectable label.

4. A kit comprising the polyclonal antibody of claim 3.

5. A method of detecting or determining one or more compounds selected from the group consisting of AB-Pinaca, AB-Pinaca pentanoic acid, 1-(5-hydroxypentyl) AB-Pinaca, 1-(4-hydroxypentyl) AB-Pinaca, and 5-fluoropentyl AB-Pinaca, in an in vitro sample or in a solution comprising:
  i. contacting the sample or solution with a detecting agent and the polyclonal antibody of claim 1, wherein both the compound and the detecting agent bind to the polyclonal antibody; and
  ii. detecting or determining the amount of detecting agent bound to the polyclonal antibody.

6. The method of claim 5, wherein the polyclonal antibody is adsorbed on or attached to a solid state device.

7. The method of claim 6, wherein the solid state device is a ceramic biochip or microtiter plate.

8. A method of making an antibody comprising:
  administering an immunogen having the structure of:

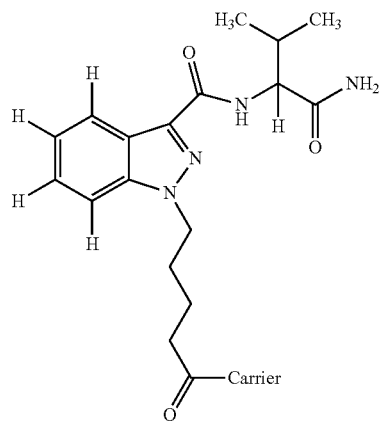

wherein "Carrier" is selected from the group consisting of Keyhole Limpet Hemocyanin (KLH) and Bovine Serum Albumin (BSA),
  to a mammal; and
  purifying the resultant antibody.

9. The method of claim 8, wherein the antibody is a polyclonal antibody.

* * * * *